(12) United States Patent
Kostrzewski et al.

(10) Patent No.: US 9,668,734 B2
(45) Date of Patent: Jun. 6, 2017

(54) IN-SITU LOADED STAPLER

(71) Applicant: Covidien LP, Mansfield, MA (US)

(72) Inventors: Stanislaw Kostrzewski, Newtown, CT (US); Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 457 days.

(21) Appl. No.: 14/279,781

(22) Filed: May 16, 2014

(65) Prior Publication Data
US 2015/0327862 A1 Nov. 19, 2015

(51) Int. Cl.
*A61B 17/072* (2006.01)
*A61B 90/00* (2016.01)

(52) U.S. Cl.
CPC .......... *A61B 17/07207* (2013.01); *A61B 2017/07228* (2013.01); *A61B 2017/07271* (2013.01); *A61B 2017/07278* (2013.01); *A61B 2090/0814* (2016.02)

(58) Field of Classification Search
CPC ............................ A61B 17/068; A61B 17/072
USPC .................................. 227/19, 176.1; 606/219
See application file for complete search history.

(56) References Cited

U.S. PATENT DOCUMENTS

| | | |
|---|---|---|
| 3,650,453 A | 3/1972 | Smith, Jr. |
| 3,717,294 A | 2/1973 | Green |
| 3,837,555 A | 9/1974 | Green |
| 4,612,933 A | 9/1986 | Brinkerhoff et al. |
| 4,892,244 A | 1/1990 | Fox et al. |

(Continued)

FOREIGN PATENT DOCUMENTS

| | | |
|---|---|---|
| EP | 0156774 A2 | 10/1985 |
| EP | 2090241 A1 | 8/2009 |

(Continued)

OTHER PUBLICATIONS

European Search Report dated Jan. 7, 2016, issued in European Application No. 15167796.

(Continued)

*Primary Examiner* — Nathaniel Chukwurah

(57) ABSTRACT

A stapling device is described which includes a tool assembly having an anvil assembly and a cartridge assembly movably supported in relation to the anvil assembly. The cartridge assembly includes a cartridge body defining a tissue contact surface and a plurality of retention slots which open onto the tissue contact surface. The cartridge body defines a plurality of recesses wherein each of the recesses is associated with one of the plurality of retention slots. A staple magazine is positioned within each of the recesses, and includes a plurality of staples. At least one biasing member is supported adjacent each of the recesses and is positioned to urge the staple magazine towards a respective one of the retention slots. A plurality of pushers is movably supported within the cartridge body between a lower position and a raised position. Each of the plurality of pushers is positioned to engage and eject at least one of the staples of the staple magazine from the retention slots. The at least one biasing member is positioned to obstruct movement of the pusher from the lower position to the raised position after the plurality of staples of the staple magazine have been ejected from a respective one of the retention slots.

19 Claims, 21 Drawing Sheets

(56) References Cited

U.S. PATENT DOCUMENTS

| | | | |
|---|---|---|---|
| 4,951,860 | A | 8/1990 | Peters et al. |
| 4,955,959 | A | 9/1990 | Tompkins et al. |
| 5,246,156 | A | 9/1993 | Rothfuss et al. |
| 5,313,935 | A | 5/1994 | Kortenbach et al. |
| 5,413,267 | A | 5/1995 | Solyntjes et al. |
| 5,415,335 | A | 5/1995 | Knodell, Jr. |
| 5,472,132 | A | 12/1995 | Savage et al. |
| 5,487,499 | A | 1/1996 | Sorrentino et al. |
| 5,709,334 | A | 1/1998 | Sorrentino et al. |
| 5,752,644 | A | 5/1998 | Bolanos et al. |
| 5,865,361 | A | 2/1999 | Milliman et al. |
| 5,893,506 | A | 4/1999 | Powell |
| 5,991,355 | A | 11/1999 | Dahlke |
| 6,079,606 | A | 6/2000 | Milliman et al. |
| 6,109,500 | A | 8/2000 | Alli et al. |
| 7,934,631 | B2 * | 5/2011 | Balbierz ............ A61B 17/068 227/176.1 |
| 7,954,683 | B1 | 6/2011 | Knodel et al. |
| 7,963,432 | B2 | 6/2011 | Knodel et al. |
| 8,070,033 | B2 | 12/2011 | Milliman et al. |
| 8,499,993 | B2 | 8/2013 | Shelton, IV et al. |
| 2005/0222616 | A1 | 10/2005 | Rethy et al. |
| 2011/0192881 | A1 | 8/2011 | Balbierz et al. |
| 2011/0245578 | A1 | 10/2011 | Wazer et al. |
| 2011/0295269 | A1 | 12/2011 | Swensgard et al. |

FOREIGN PATENT DOCUMENTS

| | | |
|---|---|---|
| EP | 2130498 A1 | 12/2009 |
| EP | 2332471 A1 | 6/2011 |
| EP | 2540231 A2 | 1/2013 |
| EP | 2687163 A1 | 1/2014 |
| EP | 2722009 A2 | 4/2014 |
| WO | 2010/054404 A1 | 5/2010 |

OTHER PUBLICATIONS

European Office Action dated Sep. 21, 2015, issued in EP Application No. 15167796.

European Search Report in related application No. EP 13 17 6778 dated Oct. 28, 2013.

* cited by examiner

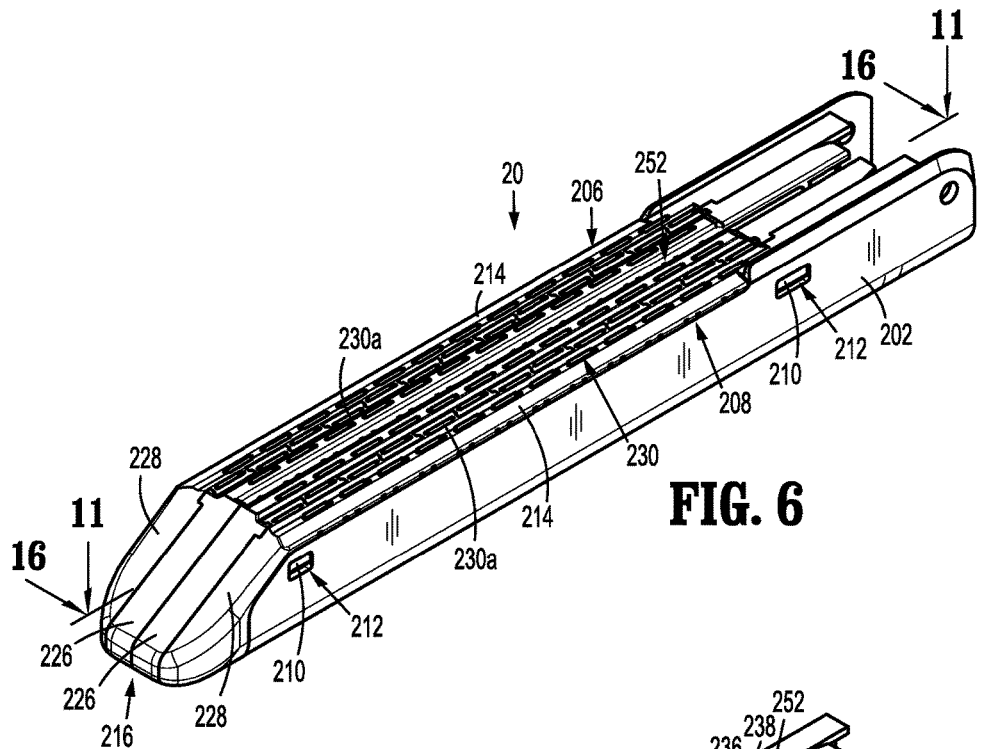
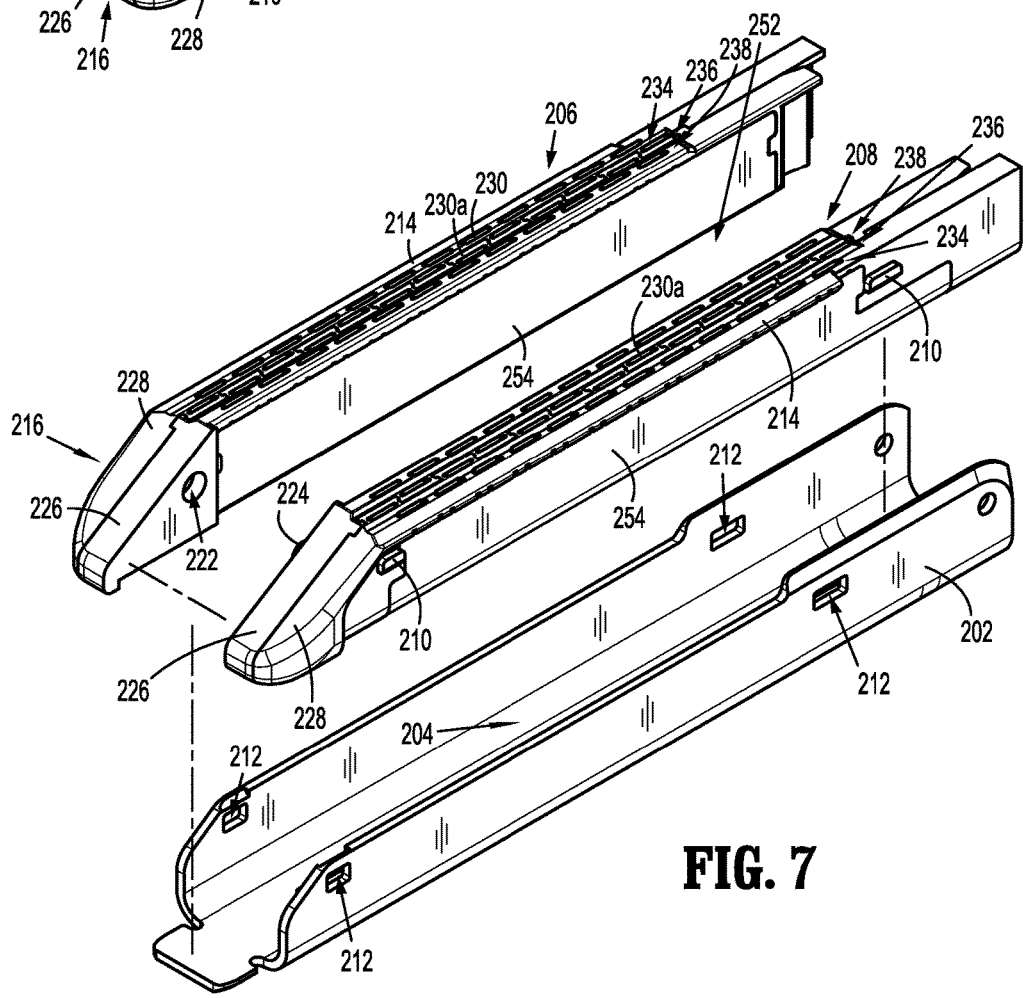

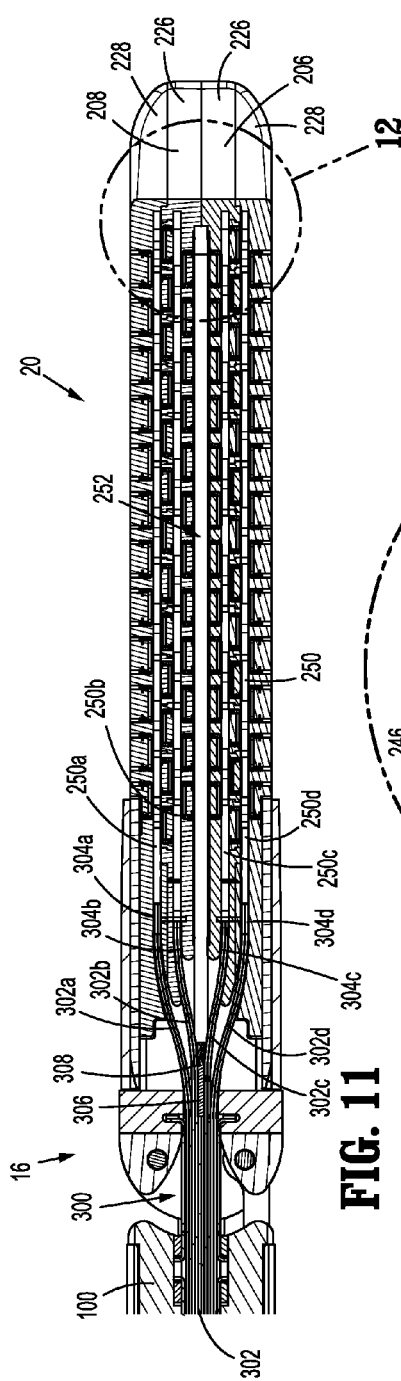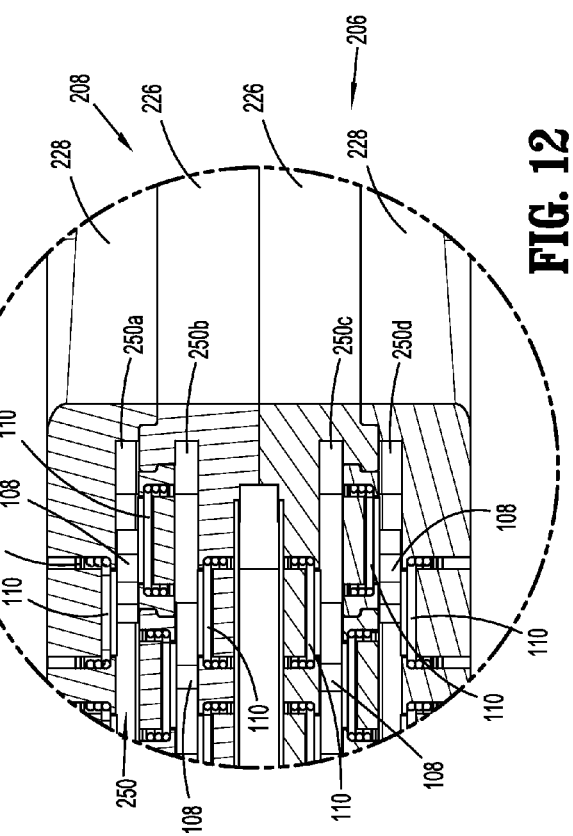
FIG. 11
FIG. 12

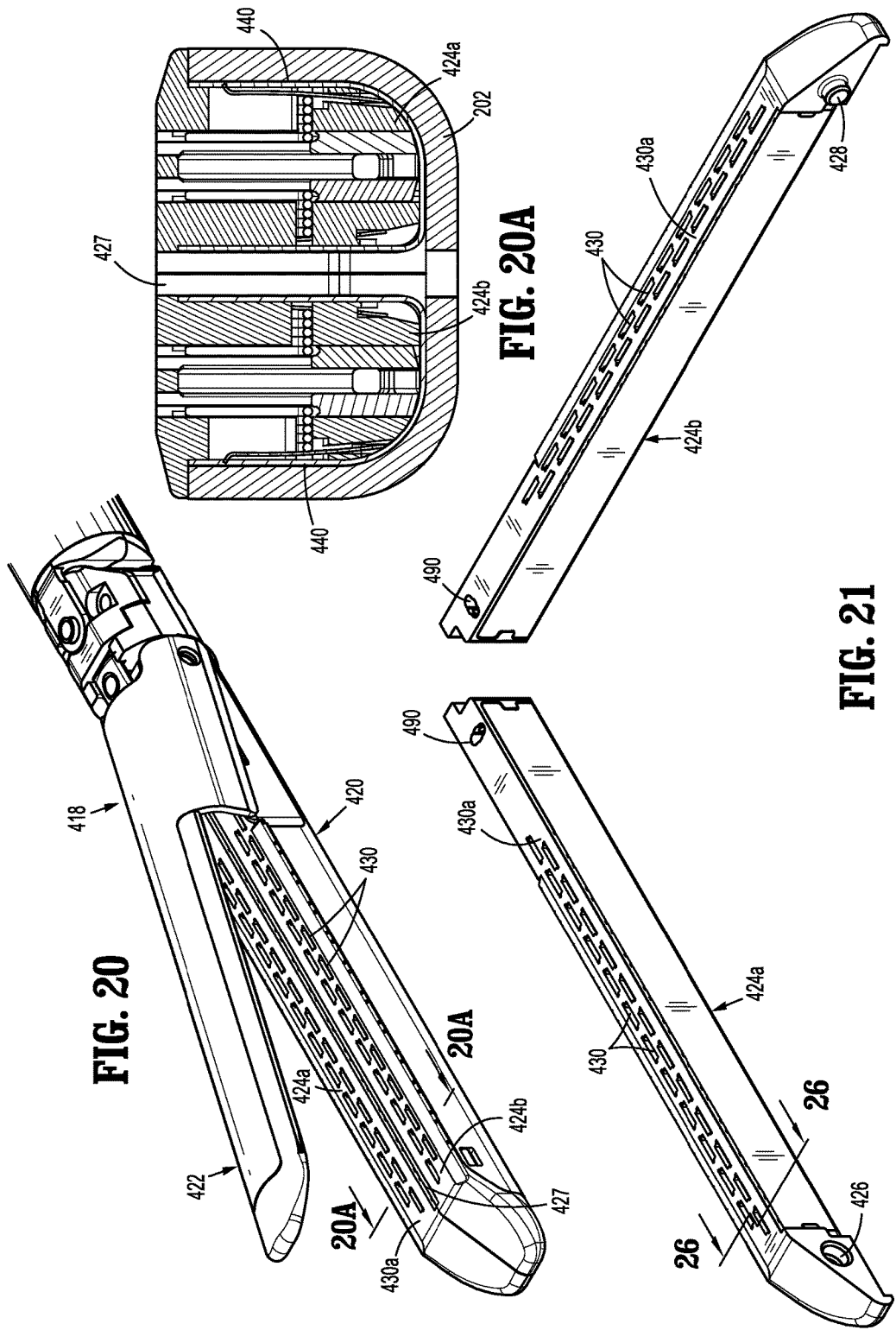

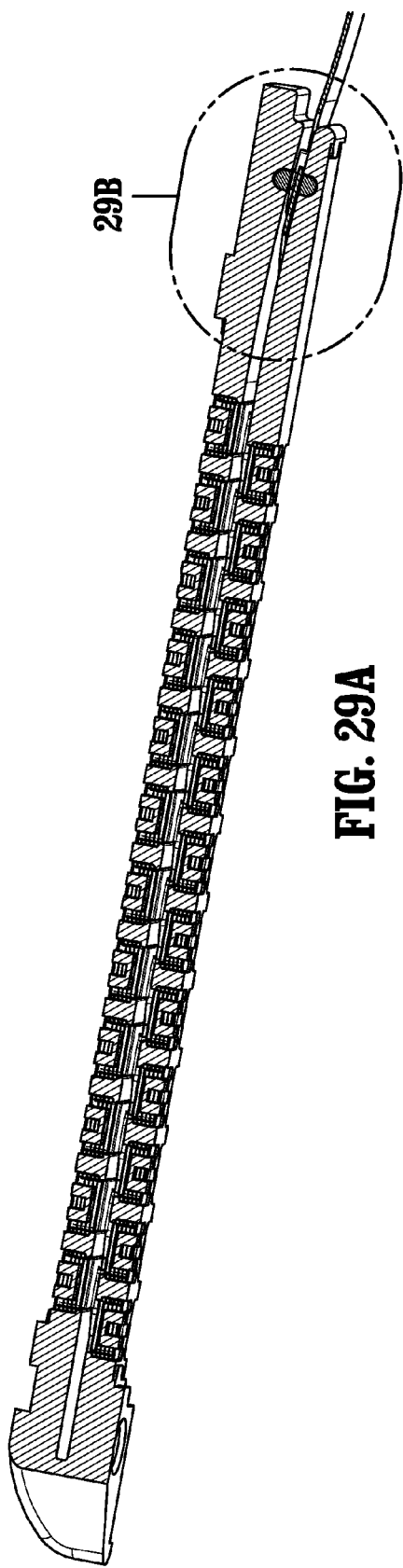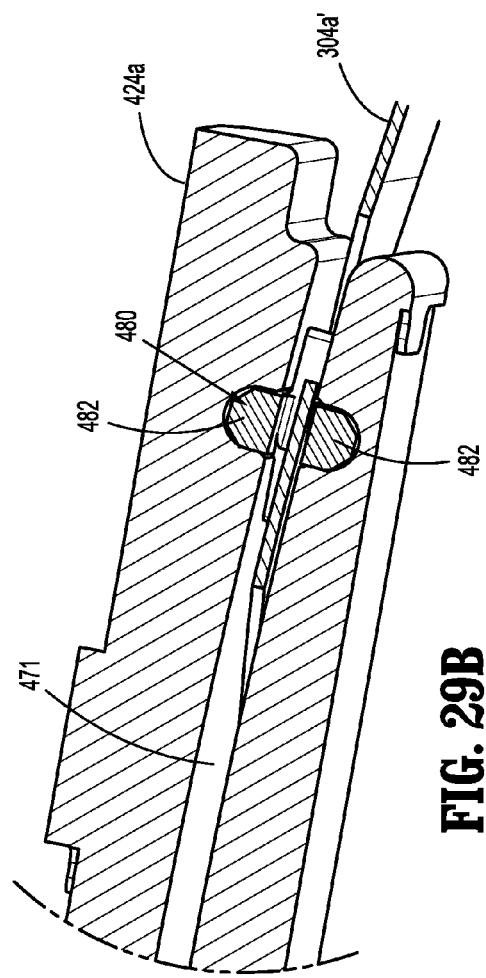
FIG. 29A
FIG. 29B

IN-SITU LOADED STAPLER

TECHNICAL FIELD

This application relates to a surgical stapling device, and more particularly, to a cartridge assembly for use with a stapling device which includes a magazine for reloading the surgical stapling apparatus in-situ and a lockout for preventing operation of the stapling device when the magazine has been depleted.

BACKGROUND

Surgical devices that grasp and clamp tissue between opposing jaw structure and, subsequently join cut and fasten the tissue are well known in the art. Such devices can include two elongated members which are used to capture or clamp tissue. Typically, one of the members carries a staple cartridge which houses a plurality of staples while the other member has an anvil that defines a surface for forming the staples as the staples are driven from the staple cartridge. Generally, the stapling operation is effected by a cam bar, a drive sled or other similar mechanism having a cam member that travels longitudinally through the staple cartridge and acts upon staple pushers to sequentially eject the staples from the staple cartridge. The cam member is moved into engagement with the staple pushers which are located within the grooves and are positioned in such a manner so as to be contacted by the longitudinally moving cam member to effect ejection of the staples from the staple cartridge of the surgical device.

Typically, surgical stapling devices include a staple cartridge or disposable unit (DLU) that must be replaced after each time the stapling device is fired for subsequent reuse of the device. In endoscopic or laparoscopic procedures wherein surgery is performed through small incisions or through narrow cannulas inserted through the small incisions in the skin, replacement of the cartridge or DLU requires removal of the stapling device from the incision or cannula, replacement of the cartridge or DLU and reinsertion of the stapling device into the incision or cannula. An example of an endoscopic surgical stapling device is disclosed, for example, in U.S. Pat. No. 8,070,033 to Milliman et al., the entire contents of which is incorporated herein by reference.

It would be beneficial to provide a surgical stapling device for use during laparoscopic and/or endoscopic surgical procedures that can be employed to provide multiple firings of the surgical stapling device without requiring removal of the surgical device from the incision/cannula. It would also be beneficial to provide a device having a lockout to prevent firing of the device after a supply of staples has been depleted.

SUMMARY

A tool assembly is provided which includes an anvil assembly and a cartridge assembly movably supported in relation to the anvil assembly. The cartridge assembly includes a cartridge body defining a tissue contact surface and a plurality of retention slots which open onto the tissue contact surface. The cartridge body defines a plurality of recesses, each of the recesses being associated with one of the plurality of retention slots. A staple magazine is positioned within each of the recesses and includes a plurality of staples. At least one biasing member is supported adjacent each of the recesses and is positioned to urge the staple magazine towards a respective one of the retention slots. A plurality of pushers is movably supported within the cartridge body between a lower position and a raised position. Each of the plurality of pushers is positioned to engage and eject at least one of the staples of the staple magazine from the retention slot. The at least one biasing member is positioned to obstruct movement of the pusher from the lower position to the raised position after the plurality of staples of the staple magazine has been ejected from a respective one of the retention slots.

In embodiments, each of the pushers includes at least one pusher plate and each of the at least one pusher plates is movable within a respective one of the retention slots to eject one of the plurality of staples of the staple magazine from the cartridge body.

In certain embodiments, each of the at least one pusher plates defines a notch and the at least one biasing member includes a leg. The leg is movable into alignment with the notch after the plurality of staples of the staple magazine has been ejected from the retention slot to obstruct movement of the pusher from the lower position to the raised position.

In embodiments, the at least one biasing member includes a first biasing member and a second biasing member. The first biasing member is supported within the cartridge body to engage legs of a respective one of the plurality of staples and the second biasing member is supported within the cartridge body to engage a backspan of the respective staple of the plurality of staples.

In certain embodiments, the first biasing member is U-shaped and includes a pair of legs positioned to engage the legs of the respective one of the plurality of staples.

In embodiments, the second biasing member is positioned to obstruct movement of the pusher after the plurality of staples of the staple magazine has been ejected from the respective one of the retention slots.

In certain embodiments, each of the pushers includes at least one pusher plate and is movable within a respective one of the retention slots to eject one of the plurality of staples of the staple magazine from the cartridge body.

In embodiments, each of the at least one pusher plates defines a notch and the at least one biasing member includes a leg. The leg is movable into alignment with the notch after the plurality of staples of the staple magazine has been ejected from the retention slot to obstruct movement of the pusher from the lower position back to the raised position.

In certain embodiments, the tool assembly includes a firing cam having a first blade and a second blade which define a camming slot. The firing cam is movable between a retracted position and an advanced position within the cartridge body such that the camming slot sequentially receives the plurality of pushers and moves the pushers between the lower position and the raised position as the firing cam translates between the retracted position and the advanced position.

In embodiments, each of the plurality of pushers includes at least one pusher plate which is movably supported within a respective one of the plurality of retention slots and a pusher base which is positioned to be received within the camming slot of the firing cam.

In certain embodiments, the cartridge assembly includes a cam separator and the cartridge body defines a vertical channel. The cam separator is supported for movement within the vertical channel and is positioned within the camming slot of the firing cam when the firing cam is in the retracted position to maintain separation of the first and second blades of the firing cam.

In embodiments, the cartridge body includes a first body half and a second body half. Each of the first and second body halves defines a plurality of retention slots and a plurality of recesses, wherein each of the plurality of recesses houses a staple magazine.

In certain embodiments, the first and second body halves of the cartridge body are supported within a carrier channel.

In embodiments, the cartridge assembly includes a first support channel and a second support channel. The first and second body halves are positioned within the first and second support channels and the first and second support channels are supported in the carrier channel of the carrier.

A tool assembly is also provided which includes an anvil assembly and a cartridge assembly including a cartridge body defining a plurality of retention slots and a plurality of recesses. Each of the plurality of recesses houses a staple magazine including a plurality of staples. A plurality of pushers is provided. Each of the plurality of pushers is associated with at least one of the retention slots. A firing cam is movable between a retracted position and an advanced position within the cartridge body and has a first blade and a second blade. The first and second blades define a camming slot which is configured to receive the plurality of pushers to effect movement of the pushers between a lower position and a raised position. A cam separator is supported within a vertical channel defined in the cartridge body. The cam separator is positioned within the camming slot of the firing cam when the firing cam is in a retracted position to maintain spacing between the first and second blades.

In certain embodiments, at least one biasing member is supported adjacent each of the recesses. The at least one biasing member is positioned to urge the staple magazine towards a respective one of the retention slots.

In embodiments, the at least one biasing member is positioned to obstruct movement of the pusher from the lower position to the raised position after the plurality of staples of the staple magazine has been ejected from a respective one of the retention slots.

In certain embodiments, each of the pushers includes at least one pusher plate and each of the at least one pusher plates is movable within a respective one of the retention slots to eject one of the plurality of staples of the staple magazine from the cartridge body.

In embodiments, each of the at least one pusher plates defines a notch and the at least one biasing member includes a leg, the leg being movable into alignment with the notch after the plurality of staples of the staple magazine has been ejected from the retention slot to obstruct movement of the pusher from the lower position to the raised position.

BRIEF DESCRIPTION OF DRAWINGS

The accompanying drawings, which are incorporated in and constitute a part of this specification, illustrate embodiments of the disclosure and, together with a general description of the disclosure given above and the detailed description of the embodiments given below, serve to explain the principles of the disclosure, wherein:

FIG. 6 is a perspective view of the cartridge assembly of the disposable loading unit of FIG. 3;

FIG. 7 is a exploded view of the cartridge assembly of FIG. 6, illustrating a pair of cartridges and a carrier;

FIG. 11 is a cross-sectional view of the cartridge assembly of FIG. 6, taken along section line 11-11;

FIG. 12 is an enlarged view of the distal end portion of the cartridge assembly of FIG. 11 indicated by the area of detail 12;

FIG. 20 is a side perspective view of an alternate embodiment of the tool assembly of the presently disclosed surgical stapling apparatus;

FIG. 20A is a cross-sectional view taken along section line 20A-20A of FIG. 20;

FIG. 21 is a side perspective view of a cartridge body of the cartridge assembly of the tool assembly shown in FIG. 20 with the cartridge separated into two body halves;

FIG. 29A is a cross-sectional view taken along section line 29A-29A of FIG. 29;

FIG. 29B is an enlarged view of the indicated area of detail shown in FIG. 29A;

DETAILED DESCRIPTION OF EMBODIMENTS

Embodiments of the presently disclosed surgical stapling apparatus will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Figure 1:
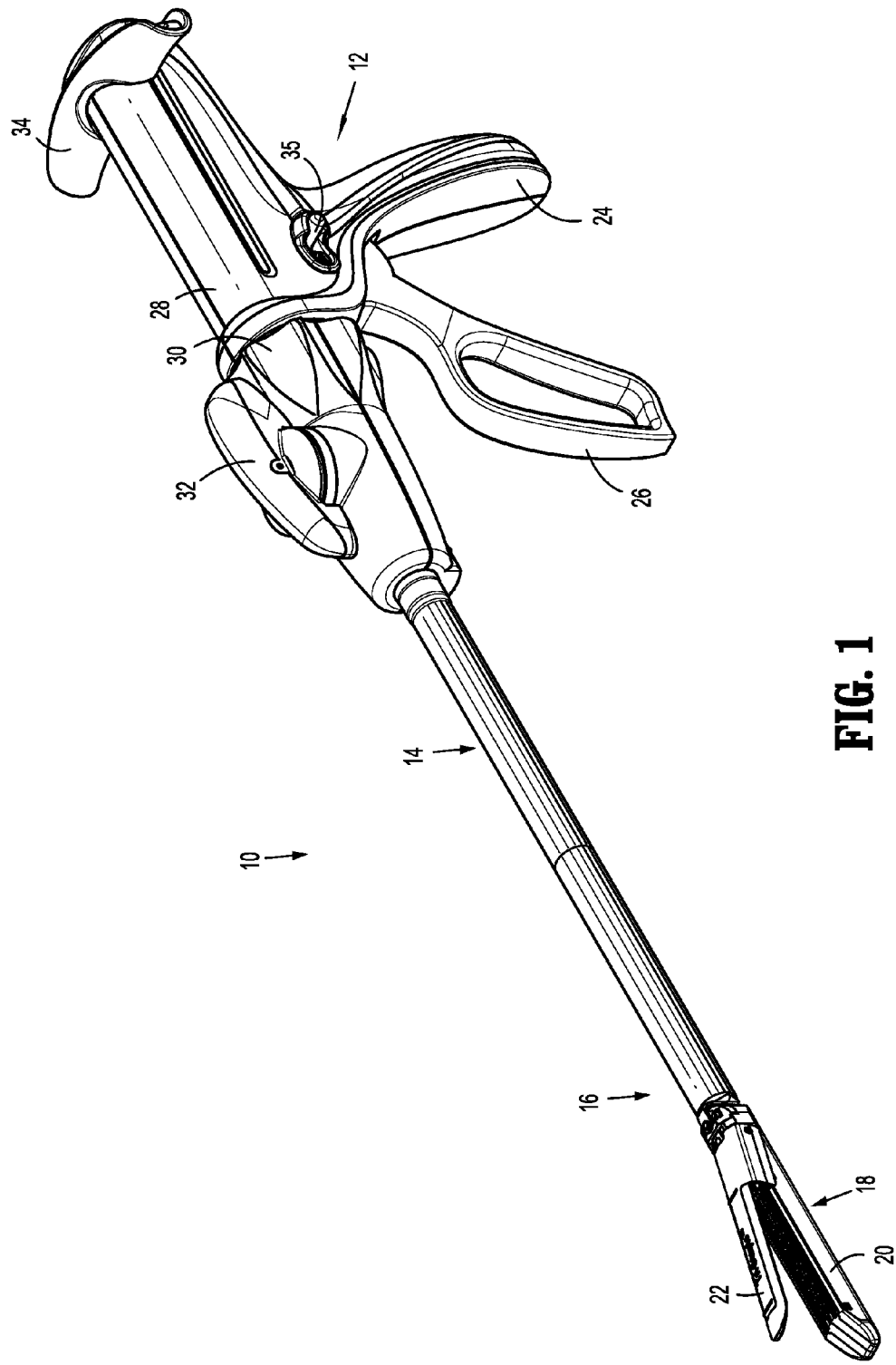
FIG. 1 is a perspective view of an exemplary surgical stapling apparatus according to the present disclosure.
Figure 2:
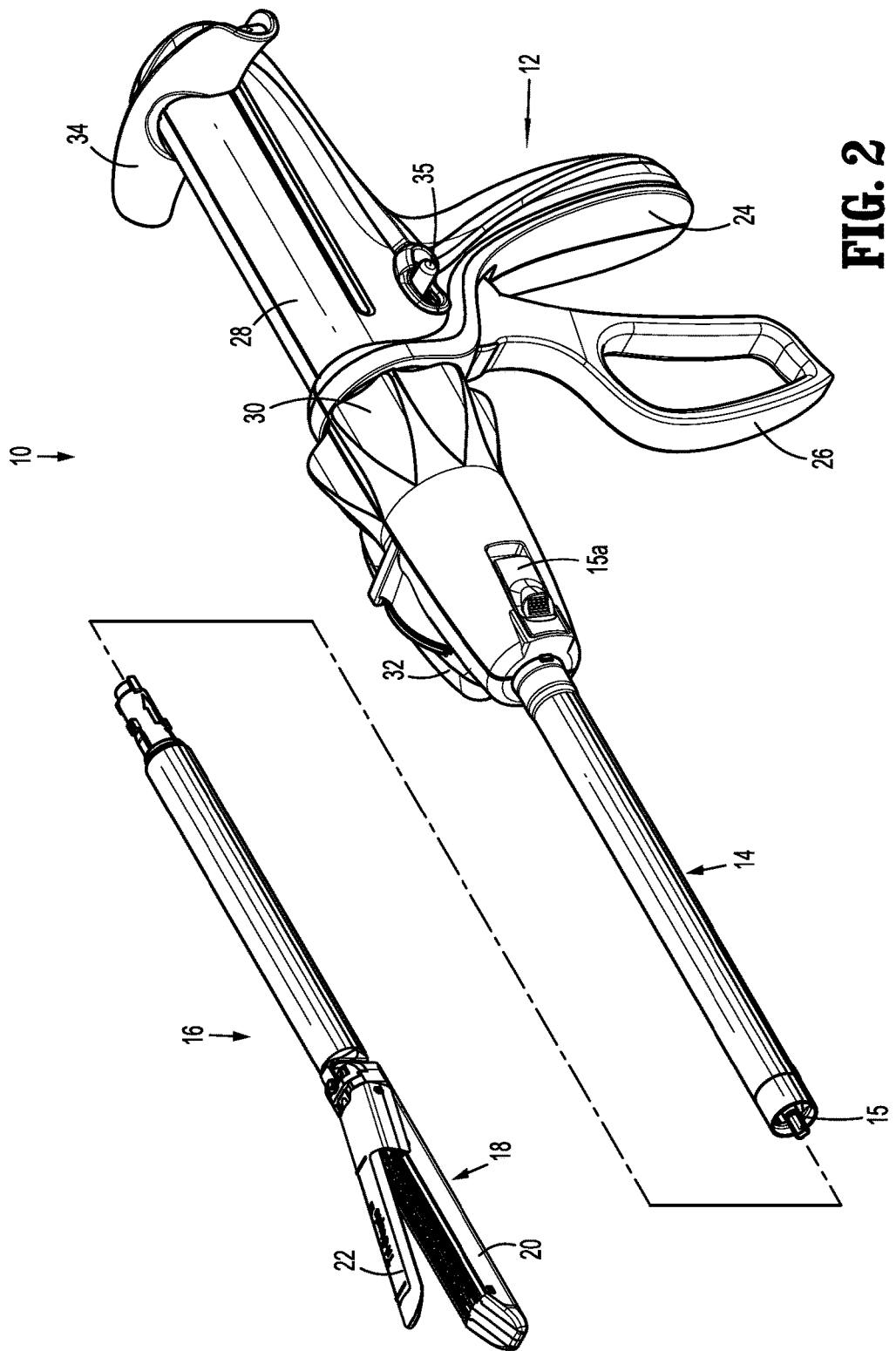
FIG. 2 is a perspective view of the surgical stapling apparatus of FIG. 1 with the disposable loading unit detached and the shaft rotated 90°.

FIGS. 1 and 2 illustrate one embodiment of the presently disclosed surgical stapling device 10. Briefly, surgical stapling device 10 includes a handle assembly 12, an elongated body 14 and a disposable loading unit ("DLU") 16. The DLU 16 is releasably secured to the distal end of the elongated body 14 and includes a tool assembly 18. The tool assembly 18 includes a cartridge assembly 20 which houses a plurality of staples and an anvil assembly 22 which is pivotally secured in relation to the cartridge assembly 20 between spaced and approximated positions. The handle assembly 12 includes a stationary handle 24, a movable handle 26 and a barrel portion 28. A rotatable member 30 is rotatably supported on a distal end of the barrel position 28. The rotatable member 30 supports a proximal end of the elongated body 14 and is rotatable in relation to the barrel portion 28 of the handle assembly 12 to effect rotation of the body 14 and the tool assembly 18 in relation to the handle assembly 12. The rotatable member 30 supports an articulation lever 32, and the barrel portion 28 supports a retraction member 34 and a firing release button 35. The handle assembly 12 is described in detail in, e.g., U.S. Pat. No. 8,070,033 to Milliman et al. ("the '033 patent") which is incorporated herein by reference in its entirety.

Referring to FIG. 2, the body 14 supports a control rod 15 which is coupled to a coupling member 307 (FIG. 14) of a firing cam assembly 300 of the DLU 16 which will be discussed in further detail below. A release switch 15a is provided on the rotatable member 30 of the handle assembly 12 to facilitate disengagement of the DLU 16 from the elongated body 14. For a more detailed description of the body 14, see the '033 patent which has been incorporated herein by reference.

Figure 3:
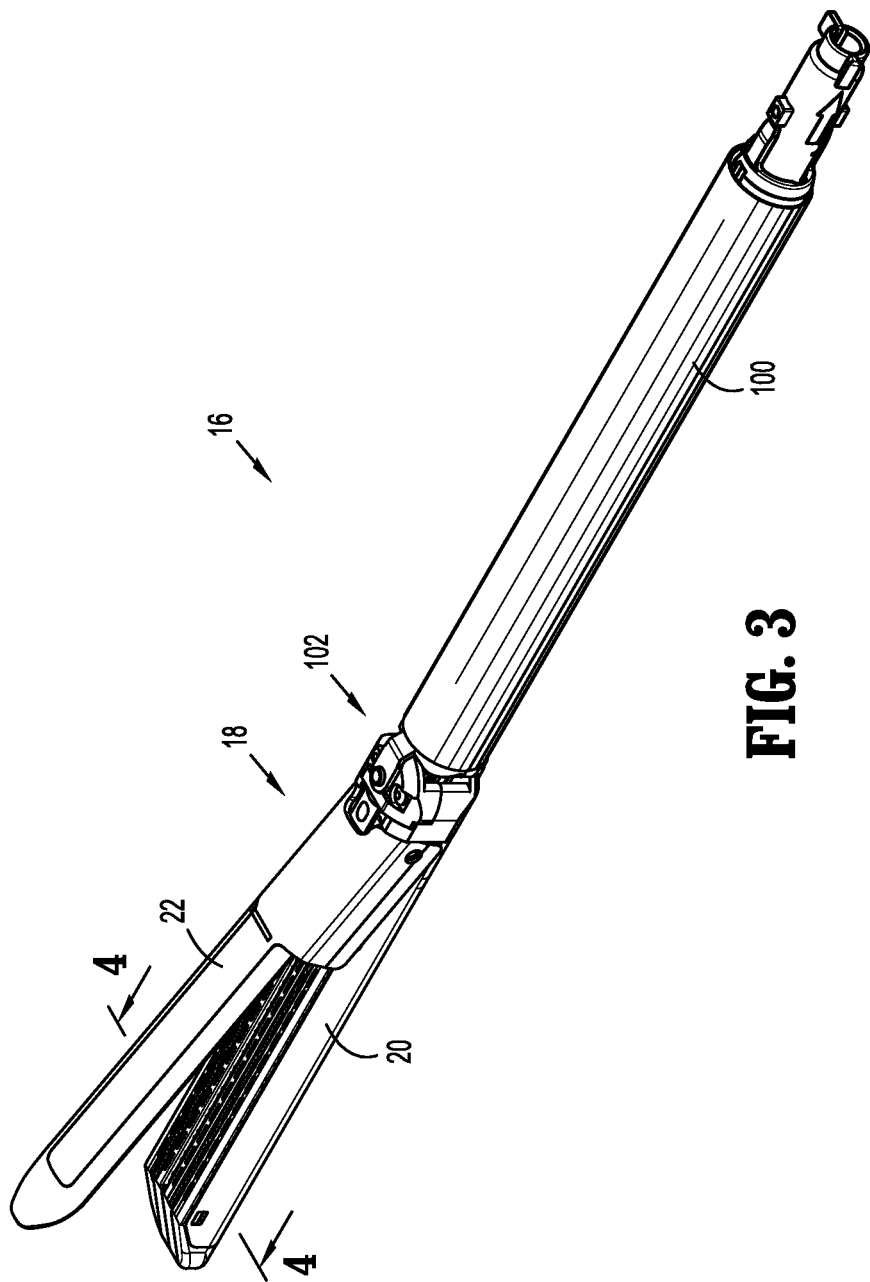
FIG. 3 a perspective view of the disposable loading unit of the surgical stapling apparatus of FIG. 1.

Referring to FIG. 3, the DLU 16 includes a proximal housing portion 100 which is adapted to releasably engage the distal end of body portion 14 (FIGS. 1 and 2). A mounting assembly 102 is pivotally secured to the distal end of housing portion 100, and is configured to engage and support the proximal end of tool assembly 18 such that pivotal movement of mounting assembly 102 about an axis perpendicular to the longitudinal axis of housing portion 100 effects articulation of tool assembly 18. See, e.g., the '033 patent for a detailed description of a mounting assembly 102.

Referring to FIGS. 3-10, tool assembly 18 includes a cartridge assembly 20 and an anvil assembly 22 pivotally connected to the cartridge assembly 20. The anvil assembly 22 defines a plurality of staple forming pockets 22a (FIG. 18), each of which is being positioned to receive a staple from the cartridge assembly 20. An example of a suitable anvil assembly 22 is described in detail in the '033 patent. Cartridge assembly 20 includes a carrier 202 which defines an elongated support channel 204 (FIG. 7) and receives a pair of staple cartridges 206, 208. Corresponding tabs 210 and slots 212 formed along staple cartridges 206, 208 and elongated support channel 204, respectively, function to retain staple cartridges 206, 208 within support channel 204. A support strut 214 formed along each staple cartridge 206, 208 is positioned to rest on a side wall of carrier 202 to stabilize staple cartridges 206, 208 within support channel 204.

With reference now to FIGS. 6 and 7, staple cartridges 206, 208 are configured to couple together at a distal end portion 216 of each of the cartridges 206, 208 to define a central longitudinal slot 252. The slot 252 facilitates passage of a knife assembly 308 (FIG. 14) through the cartridge assembly 20. An inner hole 222 formed on a surface of the distal end portion 216 of one of staple cartridges 206, 208 is configured to receive an inner tab 224 formed on a surface of the distal end portion 216 of the other of staple cartridges 206, 208. Inner hole 222 and inner tab 224 function to align staple cartridges 206, 208 when coupled together. Inner hole 222 and inner tab 224 in conjunction with tabs 210, slots 212, and struts 214 also function to maintain staple cartridges 206, 208 in a longitudinally fixed position within the elongated support channel 204 of carrier 202.

Figure 8:
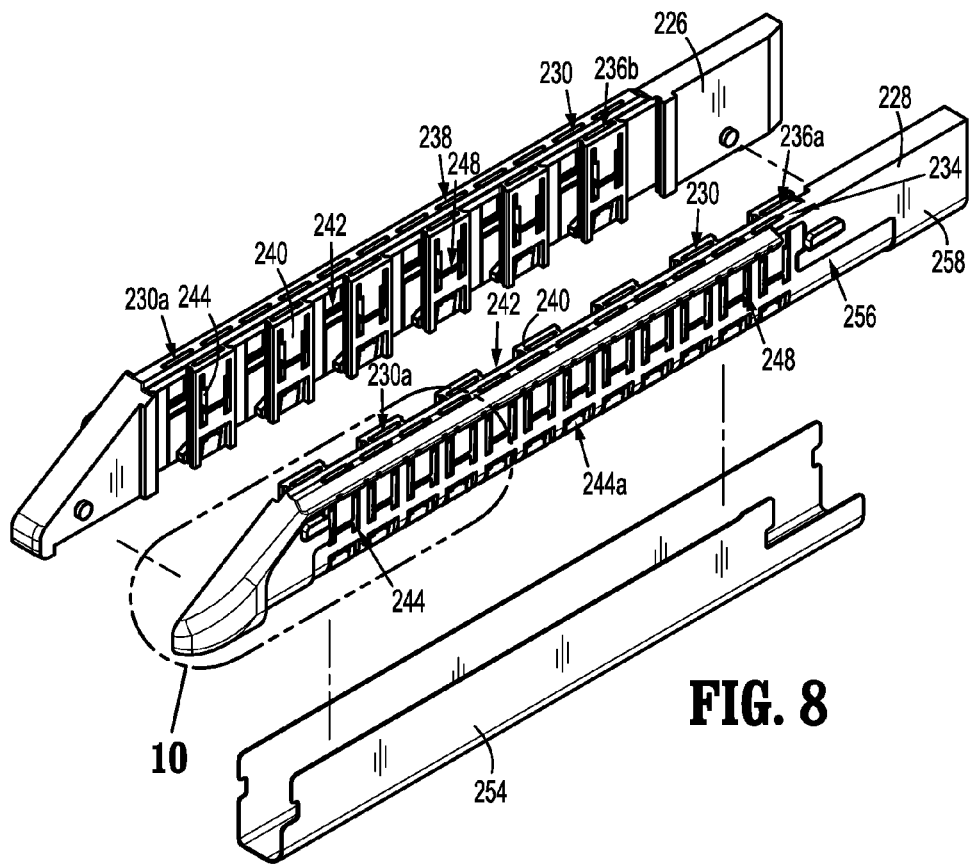
FIG. 8 is an exploded view of one of the cartridges of FIG. 7, illustrating two cartridge halves and a cartridge support channel.

Each staple cartridge 206, 208 includes an inner half and an outer half. FIG. 8 illustrates the inner and outer halves 226 and 228 of staple cartridge 208. We note that the inner and outer halves of staple cartridge 206 are mirror images of halves 226 and 228 and are not specifically described herein. The inner and outer halves 226 and 228, respectively, are configured to be coupled together. Each half 226, 228 includes retention slots 230 formed therein for receiving a plurality of staples 110 and pushers 108. Each of the staples 110 includes a pair of legs 112 having tips 110d and a backspan 110e. Retention slots 230 are aligned in rows, so that when inner half 226 and outer half 228 are coupled together, three rows of retention slots 230 are defined by each of the staple cartridges 206, 208. It is contemplated that staple cartridges 206, 208 may include fewer rows or additional rows of retention slots 230.

Outer half 228 of the staple cartridge 208 includes a first row 234 of retention slots 230 and at least a portion 236a of a second row 236 of retention slots 230. Inner half 226 of the staple cartridge 208 includes a third row 238 or retention slots 230 and at least a remaining portion 236b of the second row 236 of retention slots 230. When outer half 228 and inner half 226 are coupled together, the second row 236 of retention slots 230 is defined in part by each of portions 236a and 236b of inner half 226 and outer half 228 of the staple cartridge 208. In one embodiment, portions 236a and 236b of inner half 226 and outer half 228 of the staple cartridge 208 alternately define the retention slots 230 of second row 236 as illustrated in FIG. 8.

Each of inner half 226 and outer half 228 of the staple cartridge 208 includes a plurality of flanges 240 and a plurality of channels 242. Each flange 240 defines a retention slot 230 of the second row 236. Channels 242 are configured to receive flanges 240 when the inner half 226 is coupled to the outer half 228 of the staple cartridge 208 such that the retention slots 230 of the second row 236 are longitudinally aligned. Channels 242 and flanges 240 may alternate along the length of each of inner half 226 and outer half 228, as illustrated in FIG. 8. Alternatively, retention slots 230 of flanges 240 of each of inner and outer halves 226 and 228 may be slightly offset from a longitudinal axis such that retention slots 230 of flanges 240 of respective inner and outer halves 226 and 228 are not substantially longitudinally aligned.

Referring now to FIGS. 6-8, each cartridge 206, 208 includes a cartridge support channel 254 dimensioned and configured to receive inner and outer halves 226 and 228. Cartridge support channel 254 is configured to maintain inner and outer halves 226 and 228 in engagement in longitudinal alignment with one another. Inner and outer halves 226 and 228 include recessed sections 256 dimensioned and configured for receiving cartridge support channel 254 such that cartridge support channel 254 is substantially aligned with side surfaces 258 of inner and outer halves 226 and 228. This assists in maintaining inner and outer halves 226, 228 coupled together without adding additional width to each cartridge 206, 208 thereby maintaining a minimal width of the overall cartridge assembly 20.

Referring again to FIG. 4, in embodiments, the cartridges 206, 208 each include a tissue contacting surface 104 that is stepped. For example, an outer tissue contacting surface 104a, an intermediate tissue contacting surface 104b, and an inner tissue contacting surface 104c form a stepped configuration. Each tissue contacting surface 104a-104c has a different height from one another as measured from a bottom surface 106 of support channel 254. Specifically, tissue contacting surfaces 104a-104c are planar surfaces that are substantially parallel to one another, but are not co-planar with one another. A first wall surface interconnects tissue contacting surfaces 104a and 104b, while a second wall surface interconnects tissue contacting surfaces 104b and 104c. The first and second wall surfaces are planar structures wherein each wall surface defines an axis with respect to the planes defined by the tissue contacting surfaces 104a-104c. In one embodiment, inner tissue contacting surface 104c is defined on inner half 226 of each cartridge 206, 208, outer tissue contacting surface 104a is defined on outer half 228 of each cartridge 206, 208, and intermediate tissue contacting surface 104b is defined by the flanges 240 of inner half 226 and outer half 228 when inner and outer halves 226, 228 are coupled together.

Figure 4:
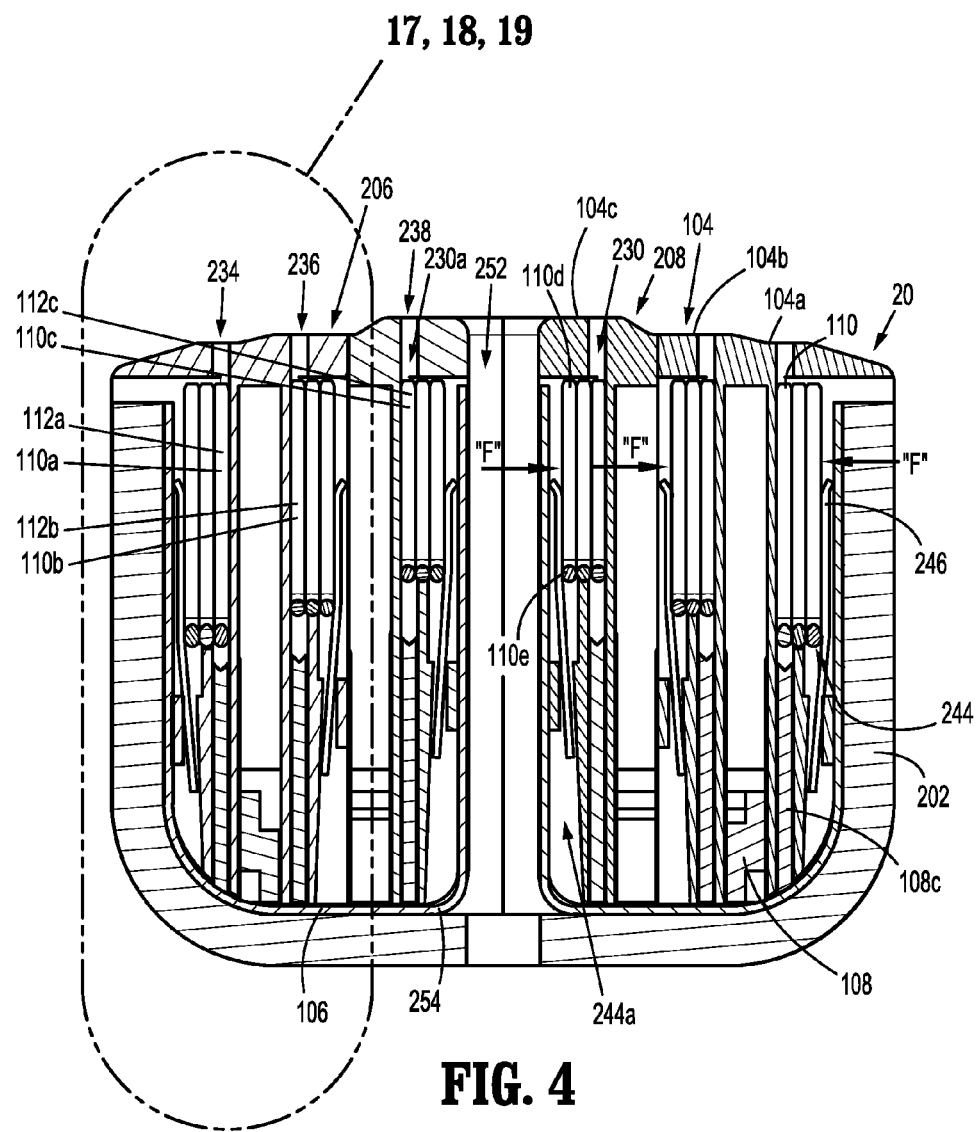
FIG. 4 is a cross-sectional view of the disposable loading unit of FIG. 3 taken along section line 4-4.

Inner tissue contacting surface 104c has the greatest height, outer tissue contacting surface 104a has the least height, and intermediate tissue contacting surface 104b has a height between the heights of outer and inner tissue contacting surfaces 104a, 104c (see FIG. 4). While tissue contacting surfaces 104a-104c are shown as increasing in height from outer most tissue contacting surface 104a to inner most tissue contacting surface 104c, it is within the scope of the present disclosure that the heights of each tissue contacting surface can vary depending on the particular surgical procedure. For example, tissue contacting surfaces 104a-104c can increase in height from the inner most tissue contacting surface 104c to the outer most tissue contacting surface 104a, the intermediate tissue contacting surface 104b can have the greatest height, the intermediate tissue contacting surface 104b can have the least height, or at least two of tissue contacting surfaces 104a-104c can have the same height.

As seen in FIG. 4, each row retention slots 230, 234, 236, 238 may include staples 110 having different sizes. For example, legs 112a of surgical staples 110a disposed in retention slots 230 of first row 234 may have a first leg length, legs 112b of surgical staples 110b disposed in retention slot 230 of second row 236 may have a second leg length, and legs 112c of surgical staples 110c disposed in retention slot 230 of third row 238 may have a third leg length. In particular, surgical staples 110a-110c increase in height from the inner most row 238 to the outermost row 234 of each cartridge. In one embodiment, legs 112c of surgical staples 110c have a leg length of about 2.3 mm, legs 112b of surgical staples 110b have a leg length of about 3.5 mm, and legs 112a of surgical staples 110a have a leg length of about 4.1 mm. As such, inner tissue contacting surface 104c has the greatest height and retains surgical staples 110c having the shortest leg lengths, and outer tissue contacting surface 104a has the least height and retains surgical staples 110a having the longest leg lengths. Tissue contacting surface 104 step progressively downward at intermediate tissue contacting surface 104b and then again at outer tissue contacting surface 104a. It is envisioned and within the scope of the present disclosure that any number of arrangements are possible. In any of the embodiments disclosed herein, the cartridge or cartridges can include staples of different sizes or the cartridge or cartridges can have staples that are all of the same size.

Figure 5:
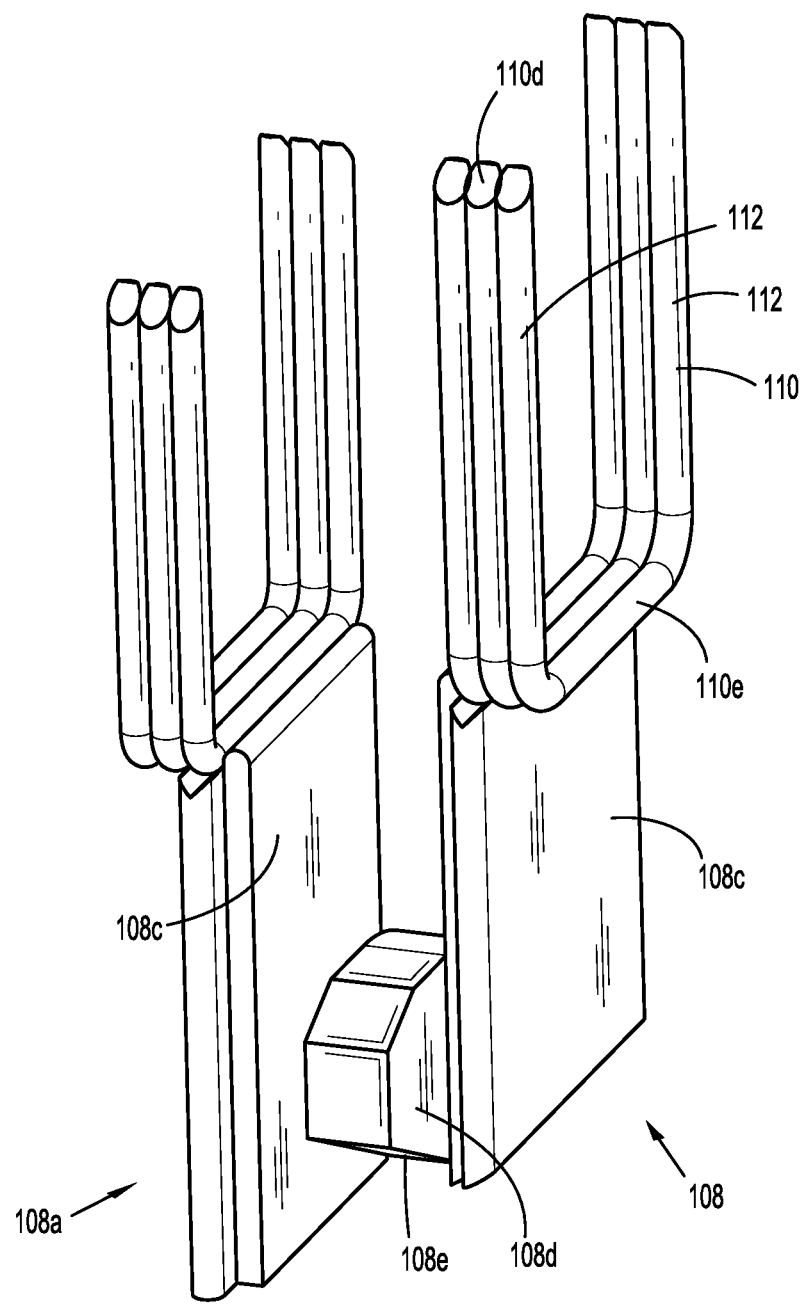
FIG. 5 is a perspective view of a two plate pusher in accordance with the present disclosure.
Figure 9:
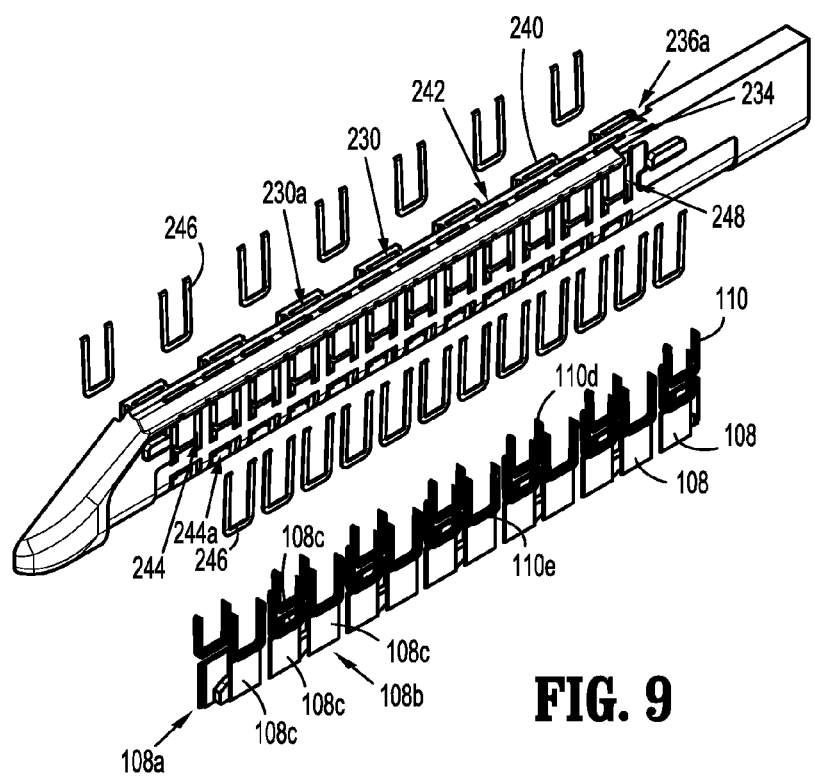
FIG. 9 is an exploded view of one of the cartridge halves of FIG. 8, illustrating the pushers, biasing members and staples removed.
Figure 10:
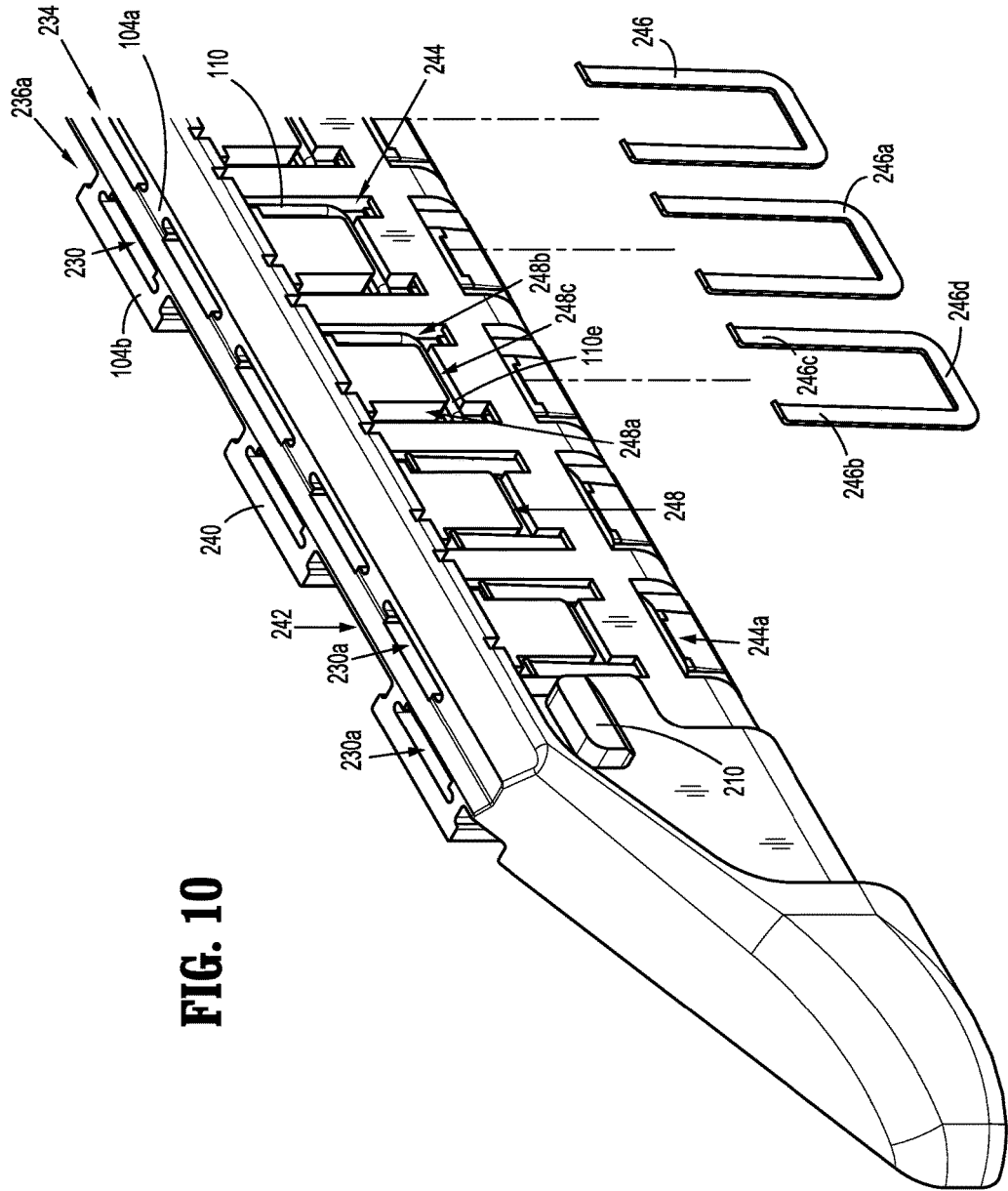
FIG. 10 is an enlarged, partially exploded, view of the distal end of one of the cartridge halves of FIG. 8 indicated by the area of detail 10.
Figure 13:
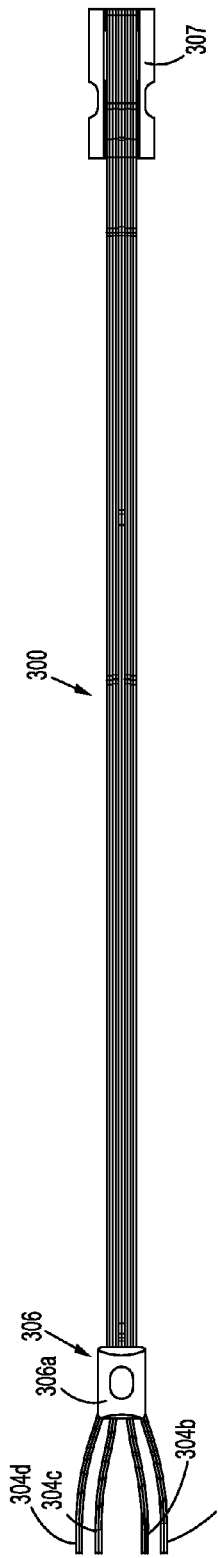
FIG. 13 is a top down view of the firing cam assembly of the cartridge assembly of FIG. 11.

With reference now to FIGS. 4 and 8-10, each retention slot 230 of inner and outer halves 226 and 228 of staple cartridge 208 has a staple magazine 244 operatively associated therewith. Each staple magazine 244 includes a recess 248 defined within the staple cartridges 206, 208, a plurality of staples 110 and a biasing member 246. The biasing member 246 is positioned to bias and urge the plurality of staples 110 towards a respective retention slot 230. As discussed above, the retention slots 230 are aligned in three different rows 234, 236 and 238 along the staple cartridges 206, 208. As discussed above, each row of retention slots 230 may receive different size staples 110. However, the staples 110 in each staple magazine 244 should be the same size. Referring now to FIG. 10, the recess 248 of the staple magazine 244 generally defines a "U" or "H" shaped channel 248 for reception of staples 110 therein. Channel 248 includes a pair of vertical segments 248a, 248b and a horizontal segment 248c. With reference to FIG. 5, each staple 110 disposed within channel 248 is maintained in a vertical orientation, with tips 110d oriented toward the tissue contacting surface 104 of the respective cartridge 206, 208. In this position, the backspan 110e of each of the staples 110 of each magazine 244 rests on horizontal segment 248c of channel 248 and the legs 112 of the staples 110 are disposed within the vertical segments 248a and 248b. The configuration of the channel 248 ensures that when a staple 110 is loaded from a magazine 244 into a respective retention slot 230, the staple 110 is properly the tissue contacting surface 104 for firing.

Each staple magazine 244 also defines a channel 244a which receives a portion of the biasing member 246 to secure the biasing member 246 in relation to the plurality of staples 110 of the staple magazine 244. Each biasing member 246 is configured to extend from the channel 244a into at least one of the vertical segments 248a and 248b of channel 248 which supports the plurality of staples 110 of each magazine 244. The biasing member 246 engages the plurality of staples 110 and urges the plurality of staples 110 towards the respective retention slot 230. It is contemplated that a separate biasing member 246 may extend into each vertical segment 248a and 248b. In the illustrated embodiment (FIG. 10), biasing member 246 includes a pair of legs 246b, 246c, and a backspan 246d. The pair of legs 246b, 246c extends into vertical segments 248a, 248b of the channel 248 when the biasing member 246 is inserted into channel 244a of magazine 244.

With reference again to FIGS. 4 and 10, when the legs 246b and 246c of the biasing member 246 are inserted through channel 244a into engagement with the plurality of staples 110, the legs 246b and 246c are deformed outwardly to bias the plurality of staples 110 to a position in vertical registration with the respective retention slot 230. The biasing member 246 is inserted into channel 244a in a substantially vertical manner and may be formed of any resilient or flexible material such as spring steel.

Alternately, the biasing member 246 may include any suitable mechanism for biasing the plurality of staples 110 disposed in each magazine 244 toward a respective retention slot 230, as described above, including, for example, springs, resilient members, or other similar biasing elements. Although illustrated as a leaf spring 246a having a substantially "U" shape, it is contemplated that the biasing member 246 may have other shapes suitable for use in biasing the staples 110 disposed in magazine 244 toward a retention slot 230.

With reference now to FIGS. 4, 5 and 9, a plurality of pushers 108 are disposed within each of the inner and outer halves 226, 228 of cartridges 206, 208. Each pusher 108 includes a pusher plate 108c which is slidably positioned within a respective retention slot 230 and is in engagement with a staple of the plurality of staples 110 of a staple magazine. Each pusher plate 108c is configured to translate through the respective retention slot 230 to urge a staple 110 disposed the retention slot 230 through a respective opening 230a in the tissue contacting surface 104, through tissue disposed between anvil assembly 22 and the cartridge assembly 20, and against staple forming pockets 22a (FIG. 18) of anvil assembly 22.

In one embodiment, as illustrated in FIG. 4, pusher plates 108c disposed in the retention slots 230 of first row 234 may have a first size, pusher plates 108c disposed in the retention slots 230 of second row 236 may have a second size, and pusher plates 108c disposed in retention slots 230 of third row 238 may have a third size. For example, pusher plates 108c of the first row 234 may be smaller than pusher plates 108c of second row 236, and pusher plates 108c of second row 236 may be smaller than pusher plates 108c of third row 238. Providing pusher plates 108c of different sizes allows pusher plates 108c to accommodate staples 110a-110c having different sizes and/or allows the pusher plates 108c to accommodate the different heights associated with the tissue contacting surfaces 104a-c associated with the rows 234, 236 and 238 of retention slots 230. Pusher plates 108c of each pusher 108 may alternatively be the same size. A tray or other member may be provided to maintain the position of the pushers prior to the staple cartridge being installed in the cartridge support channel.

Referring also to FIG. 5, each pusher 108 may be associated with one or more retention slots 230 such that upon actuation thereof, pusher 108 may fire one or more staples 110 from one or more rows of retention slots 230 through openings 230a. For example, a pusher 108a includes two pusher plates 108c and is configured to simultaneously fire two staples 110 from two adjacent rows of retention slots 230. As illustrated in FIG. 9, cartridge halves 226, 228 may include more than one type of pusher where, for example, pushers 108a, including two pusher plates 108c, that are configured for operative association with two retention slots 230 may be disposed at either end of the respective row 234, 236, 238, and pushers 108b, including three pusher plates 108c, that are configured for operative association with three retention slots 230 in two adjacent rows of retention slots 230 may be disposed between the ends of the respective rows 234, 236, 238. It is contemplated that alternate arrangements are possible where two and three retention slot pushers 108a, 108b may be included in any order. Alternatively, only one type of pusher 108 may be used, e.g., only pushers 108a configured for use with two retention slots or only pushers 108b configured for use with three retention slots. In this manner, each retention slot 230 is operatively associated with a pusher 108 that is configured to fire a fastener 110 disposed therein. It is alternatively contemplated that each pusher 108 may only include one pusher plate 108c and may only be associated with a single retention slot 230 or that each pusher 108 may include a plurality of pusher plates 108c configured for use with a plurality of retention slots 230.

Referring now to FIGS. 11-19, a firing cam assembly 300 is disposed at least partially within proximal housing 100 of DLU 16 and extends into tool assembly 18. Firing cam assembly 300 is disposed in operative communication with handle assembly 12 and is configured to translate distally and proximally through tool assembly 18 upon actuation of handle assembly 12, as will be described below in more detail.

Figure 4A:
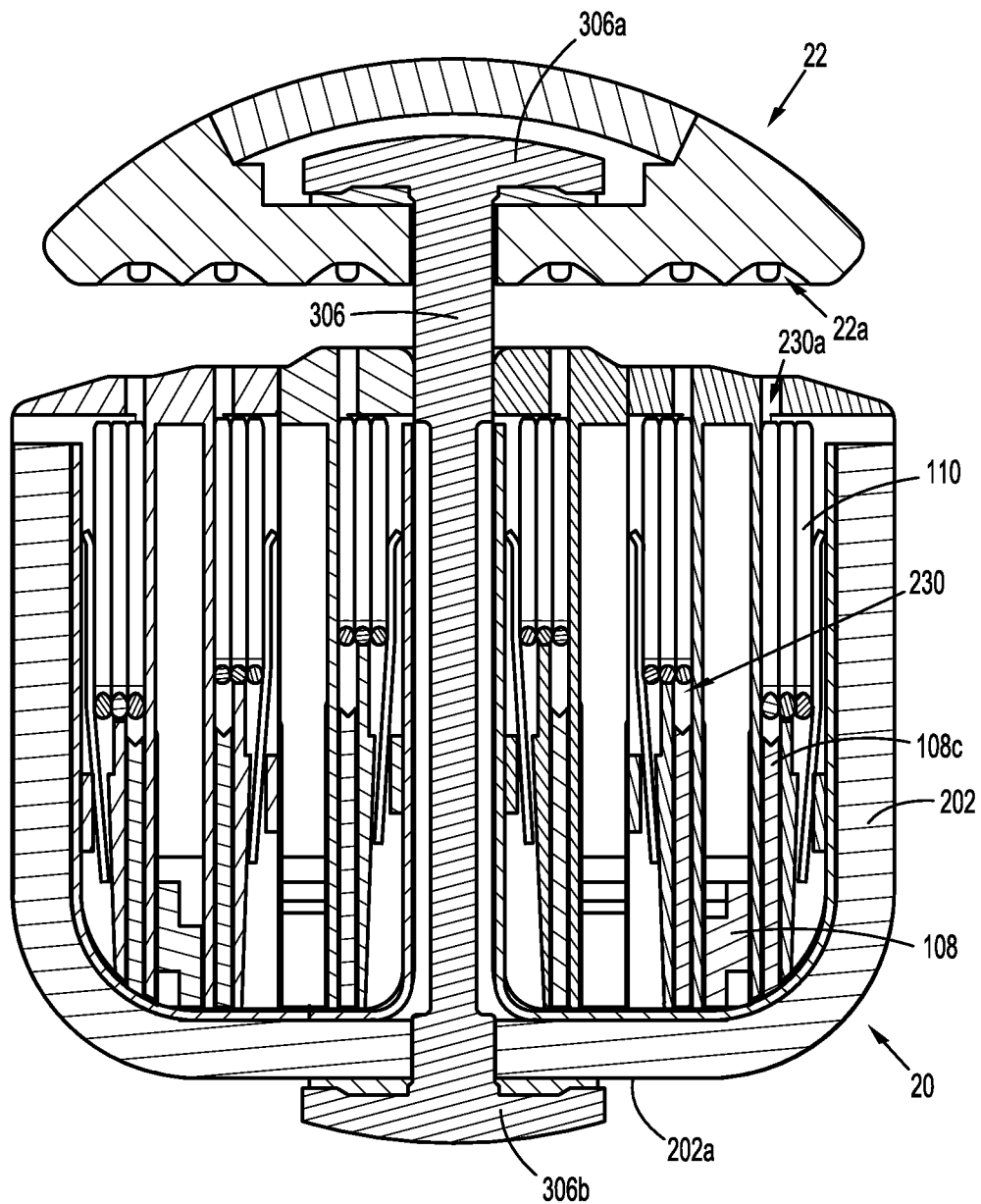
FIG. 4a is a cross-sectional view of the disposable loading unit of FIG. 3 taken along section line 4-4, illustrating the knife assembly disposed in the central channel and an anvil assembly.

With reference now to FIGS. 11-15, firing cam assembly 300 includes a plurality of drive bars 302 having firing cams 304a-d disposed at a distal end thereof and a central drive member 306 having a knife assembly 308 disposed at a distal end thereof. Knife assembly 308 defines a substantially I-shaped cross section having a top flange 306a, a bottom flange 308b and a knife blade 308c. As discussed above, a central longitudinal slot 252 defined between the staple cartridges 206, 208 extends along the length of cartridge assembly 20 to facilitate passage of central drive member 306 and knife assembly 308. With reference now to FIG. 4A, top flange 308a is configured to translate through a longitudinal slot 22b of anvil assembly 22 and bottom flange 308b is configured to translate longitudinally along an underside 202a of carrier 202.

Each half 226, 228 of each cartridge 206, 208 (FIGS. 11 and 12) includes a longitudinal slot 250 extending at least partially therethrough to accommodate passage of one of drive bars 302 and firing cams 304a-d of firing cam assembly 300 therethrough. It is contemplated, for example, that each slot 250 may accommodate passage of a single drive bar 302 and firing cam 304 or may accommodate passage of multiple drive bars 302 and firing cams 304.

With reference also to FIG. 4A, during operation of surgical stapling apparatus 10, as firing cam assembly 300 translates through DLU 16, knife assembly 308 translates through longitudinal slot 250 with top flange 306a translating through longitudinal slot 22a of anvil assembly 22 and bottom flange 306b translating along underside 202a of carrier 202 to approximate anvil assembly 22 and cartridge assembly 20 together. As knife assembly 308 translates through slot 250, knife blade 308c severs the portion of tissue that is disposed between anvil assembly 22 and cartridge assembly 20 adjacent slot 250.

With reference also to FIGS. 16-19, as firing cam assembly 300 translates through the DLU 16, drive bars 302 of firing cam assembly 300 translate through the longitudinal slots 250 of each half 226, 228 of each staple cartridge 206, 208. The firing cams 304 are advanced into sequential contact with the pushers 108 associated with retention slots 230, to cause pusher plates 108c to translate vertically within retention slots 230 and urge staples 110 from retention slots 230 through openings 230a in tissue contacting surface 104, through tissue disposed between anvil assembly 22 and the cartridge assembly 20, and against staple forming pockets 22a of anvil assembly 22 for staple forming.

Figure 19:
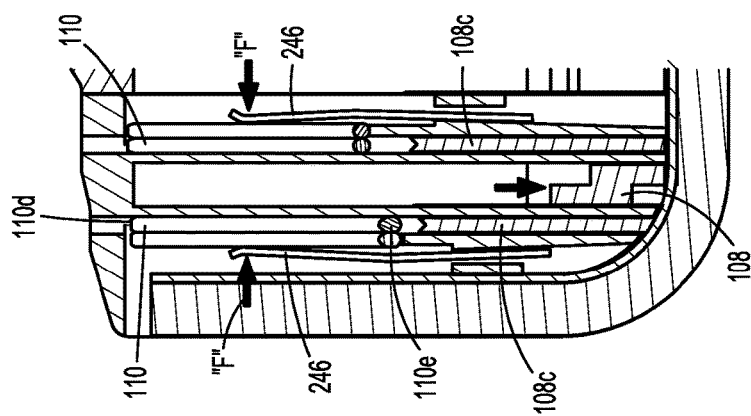
FIGS. 17-19 are enlarged cross-sectional views of the cartridge assembly of FIG. 4 indicated by the areas of detail 17, 18, 19 in FIG. 4, illustrating the firing and re-loading of a retention slot.
Figure 18:
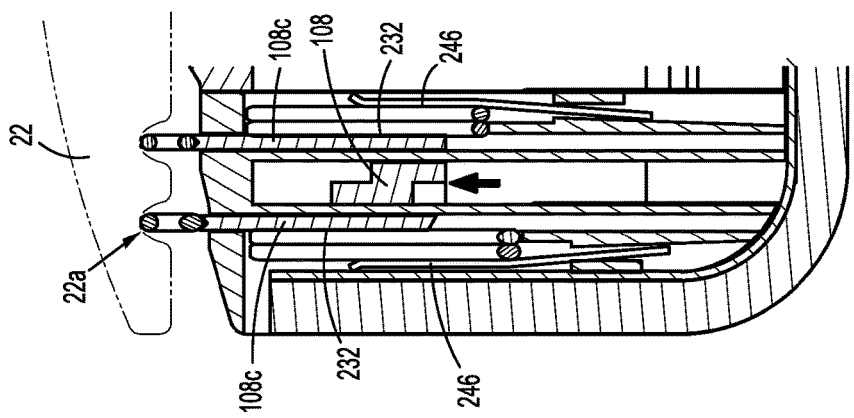
Figure 17:
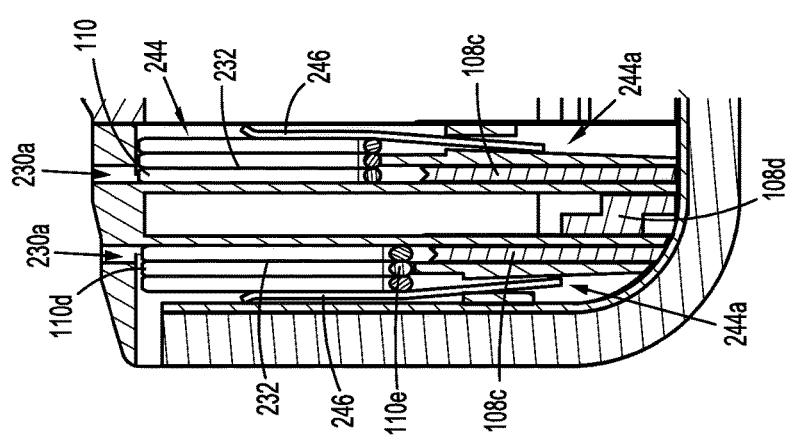

Referring now to FIGS. 17-19, during firing, as a pusher plate 108c translates through a corresponding retention slot 230 to a fired position, pusher plate 108c at least partially blocks or covers an opening 232 between retention slot 230 and magazine 244 to inhibit reloading of retention slot 230 with a new fastener 110 by magazine 244 until the firing stroke is complete. As pusher plate 108c returns to its pre-fired position at the base of retention slot 230, opening 232 is uncovered or opened to magazine 244 and receives the next staple 110 from magazine 244 due to biasing force "F" of biasing member 246. It is contemplated that the next staple 110 from magazine 244 may be at least partially received through opening 232 and within retention slot 230 as pusher plate 108c returns toward its pre-fired position where, for example, tips 110d of the next staple 110 may be received through opening 232 and within retention slot 230 before backspan 110e is received through opening 232 and within retention slot 230.

As illustrated, the drive bars 302a-d are initially disposed adjacent to one another within proximal housing 100 of the DLU 16. However, each of the drive bars 302a-d is formed of a resilient, flexible material, e.g., spring steel and must facilitate translation through longitudinal slots 250.

Referring again to FIGS. 11-16, the firing cam assembly 300 may include, for example, four pairs of drive bars 302a-302d including four pairs of corresponding firing cams 304a-304d. Each pair of drive bars 302a-302d corresponds to a respective longitudinal slot 250a-250d of cartridges 206, 208 and is translatable through a respective longitudinal slot 250a-250d to actuate pushers 108 disposed in the respective longitudinal slot 250a-250d to effect firing of staples 110 disposed in corresponding retention slots 230. Drive bars 302a-302d and central drive member 306 are coupled together at their proximal end by welding or the like. The coupling member 307 is supported in a cutout formed in the proximal end of the firing cam assembly 300 and is configured to releasably engage a control rod 15 (FIG. 2) of the stapling apparatus 10.

Figure 16:
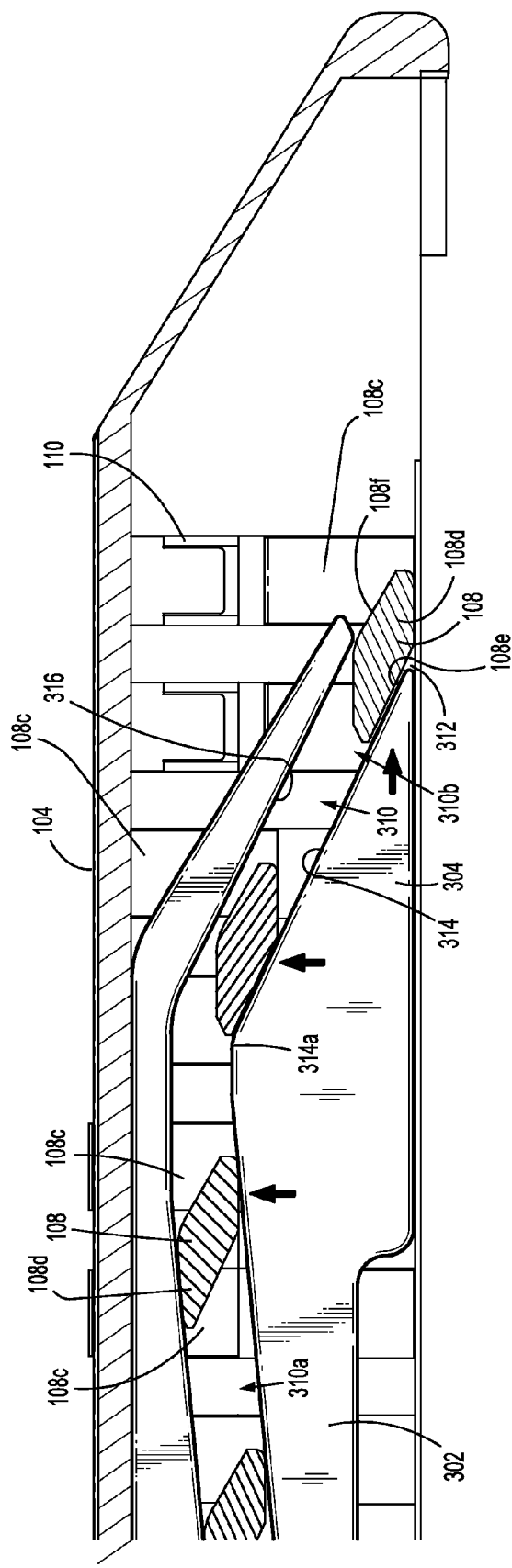
FIG. 16 is a side, cross-sectional view of the cartridge assembly of FIG. 6, taken along section line 16-16.

Referring to FIGS. 5 and 16, each pusher 108 includes a pusher base 108d having a proximal cam surface 108e and a distal cam surface 108f. Each pusher base 108d is disposed within one of longitudinal slots 250 with the proximal and distal cam surfaces 108e, 108f being configured for engagement with at least one of firing cams 304 upon distal translation thereof to cause pusher 108 to translate toward tissue contacting surface 104. Translation of pusher 108 in turn causes translation of a corresponding pusher plate 108c through a corresponding retention slot 230 toward tissue contacting surface 104 to eject staples 110 from the corresponding retention slots 230.

Referring now to FIGS. 14-19, each drive bar 302a-d and firing cam 304a-d includes a camming slot 310 having a proximal portion 310a and a distal portion 310b. Distal portion 310b includes an opening 312, a firing cam surface 314 and a retracting cam surface 316. Opening 312 is configured to receive the pusher base 108d such that the proximal cam surface 108e of pusher base 108d engages firing cam surface 314 during distal translation of the firing cam 304. Each firing cam surface 314 is sloped such that as proximal cam surface 108e of pusher base 108d slides along firing cam surface 314, pusher 108 is urged toward tissue contacting surface 104 from a pre-fired position to a fired position. As pusher 108 is urged toward tissue contacting surface 104, the corresponding pusher plate 108c translates through the corresponding retention slot 230 to drive the staple 110 disposed in the retention slot 230 through the opening 230a of tissue contacting surface 104, through tissue disposed between anvil assembly 22 and cartridge assembly 20, and against a staple forming pocket 22a of anvil assembly 22.

Once the pusher base 108d reaches the fired position at a top portion 314a of firing cam surface 314, drive bars 302a-d and firing cams 304a-d are further translated distally such that pusher base 108d slides along camming slot 310 towards proximal portion 310a. Proximal portion 310a of camming slot 310 is dimensioned such that as drive bars 302a-d and firing cams 304a-d continue to translate distally, pusher base 108d remains in the fired position. This allows the corresponding pusher plate 108c to remain in a position which at least partially blocks or covers the opening 232 of retention slot 230 (FIG. 18) to inhibit loading of the next staple 110 from the corresponding magazine 244 associated with the respective retention slot 230. Camming slot 310 extends a sufficient distance along drive bar 302 to accommodate a full firing stroke of firing cam assembly 300 where, for example, when drive bars 302a-d and firing cams 304a-d are in a distal most position, a proximal end 310c of camming slot 310 is disposed adjacent to or proximal of the proximal most pusher 108.

During refraction of firing cam assembly 300 after the firing stroke, the distal cam surfaces 108f of pushers 108 are engaged by retracting cam surface 316 of drive bars 302a-d as drive bars 302a-d and firing cams 304a-d are translated proximally. The distal cam surfaces 108f or pushers 108 are driven along retracting cam surface 316 of drive bars 302a-d toward opening 312 of camming slot 310 to return the pusher 108 from the fired position to the pre-fired position. As each pusher 108 slides along retracting cam surface 316 of firing cam 304 toward the pre-fired position, the corresponding pusher plate 108c translates toward a base of the corresponding retention slot 230 and opens up or uncovers the opening 232 of the corresponding retention slot 230 to the corresponding magazine 244. Once opening 232 is uncovered, retention slot 230 receives the next staple 110 from the magazine 244 due to the biasing force of biasing member 246. When the firing cam assembly 300 is fully retracted and each retention slot 230 has been loaded with a new staple 110 from a corresponding magazine 244, the surgical stapling apparatus 10 is ready to perform a stapling and cutting operation.

Referring now to FIGS. 4-10 the assembly of cartridge assembly 20 will now be described. A staple pusher 108 is positioned in operative association with each retention slot 230 with pusher base 108d being disposed in one of longitudinal slots 250 of each half 226, 228 of each cartridge 206, 208. Staples 110 are loaded into retention slots 230 through the "U" or "H" shaped channels 248 and the biasing members 246 are inserted into the channels 244a of the magazines 244 such that legs 246b, 246c extend into the vertical segments 248a, 248b of channels 248 and bias the staples 110 of a respective staple magazine 244 toward retention slots 230.

Once the components of each half 226, 228 of each cartridge 206, 208 have been assembled, inner and outer halves 226, 228 of each cartridge 206, 208 are joined or coupled together by positioning the flanges 240 of each half 226, 228 and into the channels 242 of each other half 226, 228 to interlock the halves 226, 228 together. The assembled inner and outer halves 226, 228 are then inserted into the cartridge support channel 254 which maintains inner and outer halves 226 and 228 in engagement with one another.

Referring now to FIGS. 6 and 7, the assembled cartridges 206, 208 are joined together at the distal end portion 216 by positioning the inner tab 224 within the inner hole 222 so as to define the central longitudinal slot 252. The joined cartridges 206, 208 are inserted into elongated support channel 204 of carrier 202 such that tabs 210 disposed on cartridges 206, 208 are positioned within the slots 212 of carrier 202 and support struts 214 of cartridges 206, 208 rest on the side walls of carrier 202. The cartridge assembly 20 is now assembled and ready for use.

The operation of surgical stapling device 10 during a surgical procedure will now be discussed with reference to FIGS. 16-19. During the surgical procedure, the surgeon attaches the loading unit 16 to the elongated body 14 (FIG. 1) and inserts the DLU 16 into the surgical site through an incision and/or cannula. The surgeon manipulates the stapling apparatus 10 to position tissue between cartridge assembly 20 and anvil assembly 22 and actuates handle assembly 12 to approximate the anvil assembly 22 with the cartridge assembly 20 and grasp the tissue. After confirming that the desired tissue is positioned between the anvil assembly 22 and the cartridge assembly 20, the surgeon actuates handle assembly 12 to drive firing cam assembly 300 distally through cartridge assembly 20 and fire the surgical staples. It is contemplated that a single actuation of handle assembly 12 by the surgeon may grasp tissue and fully fire the surgical stapling device 10. Alternatively, grasping tissue and firing of the surgical stapling device may require multiple actuations of handle assembly 12 with each actuation advancing firing cam assembly 300 a predetermined distance through DLU 16. It is contemplated that the handle portion can be a motorized handle assembly or robotically controlled actuator. Such motorized handle assembly or robotically controlled actuator can include a controller and/or power source.

As firing cam assembly 300 translates through cartridge assembly 20, each pair of drive bars 302a-302d and attached pairs of firing cams 304a-304d translate through respective longitudinal slots 250 of one of inner and outer halves 226, 228, of cartridges 206, 208. During distal translation of firing cams 304a-304d, each firing cam 304 engages a series of pusher 108 to sequentially drive the pushers 108 toward the tissue engaging surface 104 of the cartridge assembly 20 and eject staples 110 from the retention slots 230 disposed in cartridges 206, 208.

As discussed above, as each firing cam 304 engages a pusher 108, the proximal cam surface 108e of the pusher 108 engages the firing cam surface 314 of the firing cam 304 and is driven up the firing cam surface 314 from the pre-fired position to the fired position, e.g., towards tissue contacting surface 104. As the pusher 108 is driven towards tissue contacting surface 104, its respective pusher plate 108c translates through a corresponding retention slot 230 to eject a corresponding staple 110 from the corresponding retention slots 230 through a respective opening 230a in tissue contacting surface 104, through tissue disposed between anvil assembly 22 and cartridge assembly 20, and against staple forming pockets 22a of anvil assembly 22, thereby forming each staple 110. As the firing cam 304a-d continues to translate distally, pusher base 108d travels along camming slot 310 toward proximal end portion 310a and is maintained in a raised or fired position, e.g., driven toward tissue contacting surface 104, such that the corresponding pusher plate 108c blocks or covers the opening 232 between the retention slot 230 and the corresponding magazine 244. As firing cam assembly 300 translates distally, knife assembly 308 also translates distally through central longitudinal slot 252 to sever the tissue held between the cartridge assembly 20 and anvil assembly 22.

Once the firing stroke is complete, with firing cam assembly 300 disposed in a distal most position, the surgeon retracts the firing cam assembly 300, such as by withdrawing retraction member 34 (FIG. 1) proximally. As firing cam assembly 300 translates proximally through cartridge assembly 20, firing cams 304a-d are translated proximally through longitudinal slots 250 such that the distal cam surface 108f of each pusher base 108d engages the retracting cam surface 316 to drive the pusher base 108d down toward opening 312 and the pre-fired or lowered position. As each pusher base 108d is driven toward opening 312, each pusher is translated away from tissue contacting surface 104 and each pusher plate 108c is translated away from tissue contacting surface 104 toward the pre-fired position within a corresponding retention slot 230. As each pusher plate 108c is withdrawn to the pre-fired position, the opening 232 between the retention slot 230 and the corresponding magazine 244 is uncovered to allow the next staple 110 to be moved from the staple magazine 244 into a respective retention slot 230 due to the biasing force "F" (FIG. 19) of the corresponding biasing member 246. Once firing cam assembly 300 is fully translated proximally to a pre-firing position, each retention slot 230 has been reloaded and surgical stapling apparatus 10 is ready to perform a stapling and cutting procedure. In this manner, each retention slot 230 is reloaded in-situ and ready for subsequent use without requiring the surgeon to withdraw the DLU 16 from the surgical site or replace the DLU 16.

It is contemplated that each DLU 16 may be configured for multiple firing strokes.

Figure 15:
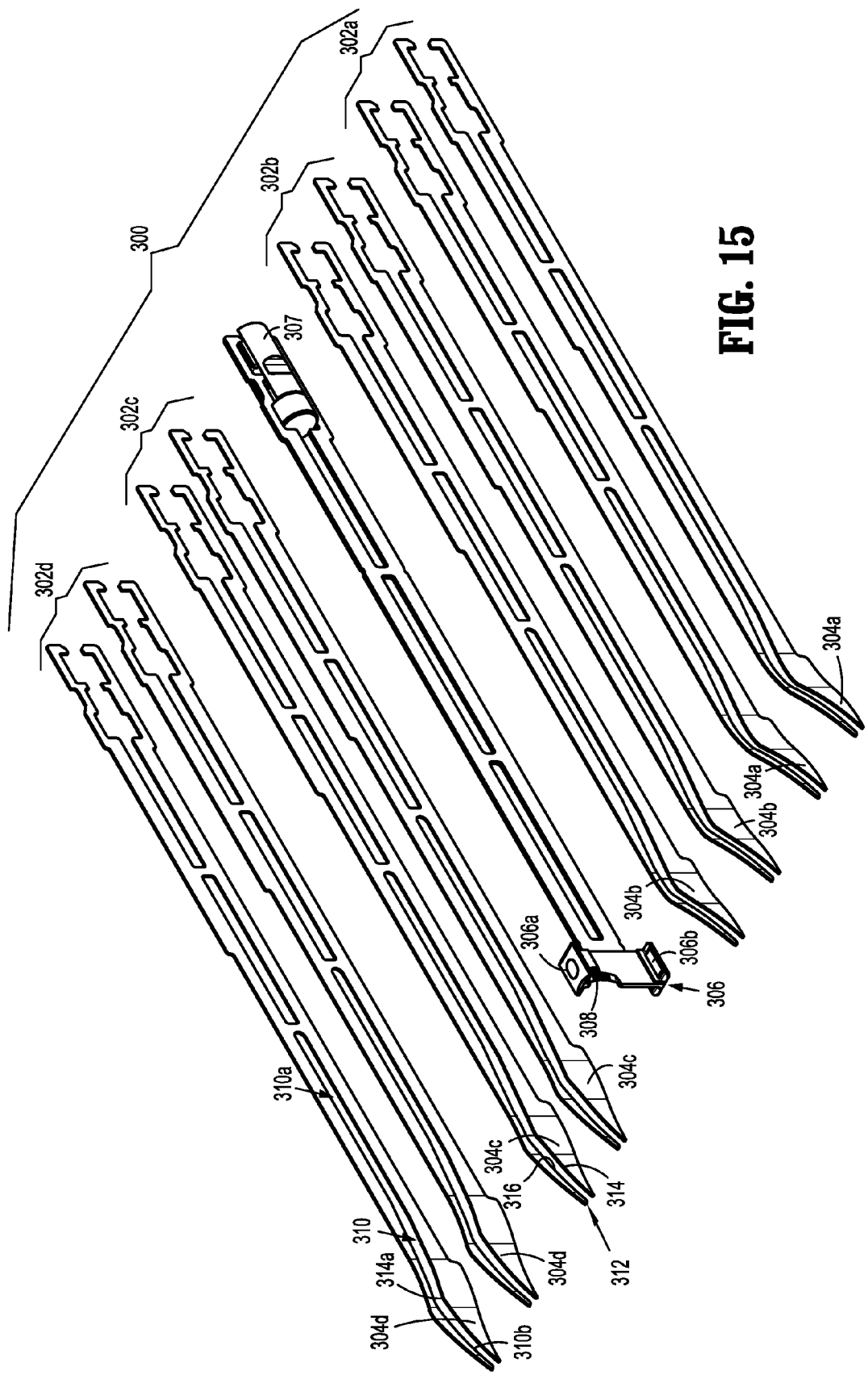
FIG. 15 is an exploded view of the firing cam assembly of FIG. 14.

In any of the embodiments disclosed herein, the drive bars 302 can be configured as more than one bar partially attached to each other. As shown in FIG. 15, each drive bar is comprised of two drive bars. Each bar can be attached, or partially attached, to at least one other adjacent bar, in any of the embodiments disclosed herein. They may be attached by adhesives or welding. For example, a drive bar comprised of two bars is welded together at the distal end, near the cam surface. Each staple pusher is driven by a pair of such cam bar assemblies, as described in above. The assembly has better flexibility and permits articulation. Welding two or more bars together gives the bar assembly more stiffness and is desirably welded near the cam surface 304. In any of the embodiments disclosed herein, a pair of relatively thinner bars is used, instead of a single relatively thicker bar, which is at least partially attached to one another.

FIGS. 20-31 illustrate an alternate embodiment of a tool assembly shown generally as 418 for use with surgical stapling apparatus 10 (FIG. 1). The tool assembly 418 includes a cartridge assembly 420 and an anvil assembly 422. The anvil assembly 422 is substantially as described above with respect to anvil assembly 22 (FIG. 1) and will not be described in further detail below. The cartridge assembly is provided to effect multiple staple firings and to lockout the cartridge assembly 420 when depleted of staples.

Figure 22:
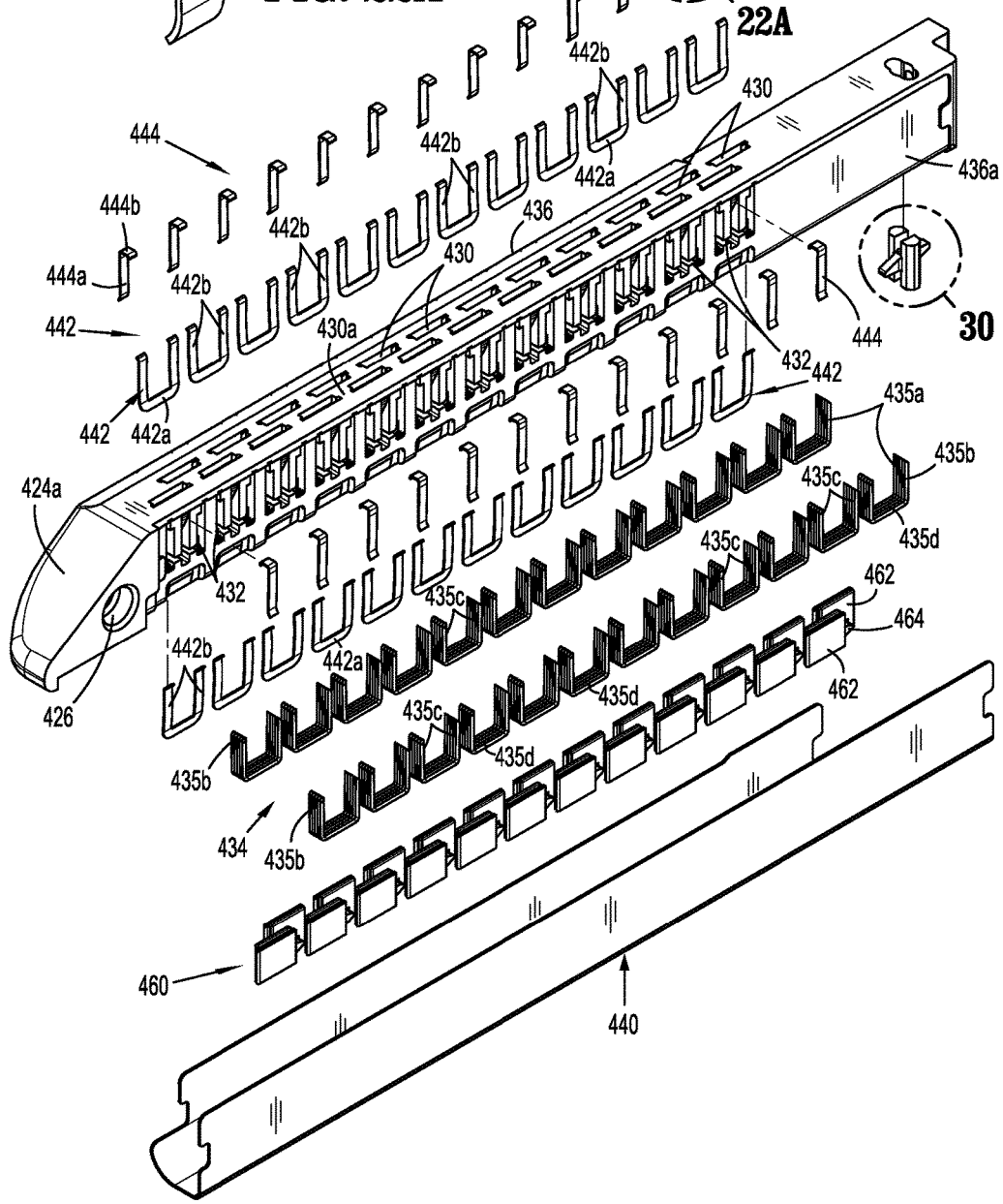
FIG. 22 is an exploded, side perspective view of one half of the cartridge body shown in FIG. 20.

Referring to FIGS. 20-22, the cartridge assembly 420 includes a first body half 424a, a second body half 424b, a pair of cartridge half support channels 440 for supporting each of first and second body halves 424a and 424b, and a carrier 202 (FIG. 20A) defining a channel for receiving the support channels 440. The first body half 424a defines a distally located hole 426 and the second body half 424*b* defines distally located tab or a protrusion 428. The tab 428 is positioned within the hole 426 to axially fix the distal end of the first body half 424*a* in relation to the second body half 424*b*. Alternately, other fastening techniques on devices can be used to secure the first and second body halves together. When the first and second body halves 424*a* and 424*b* are fixed together, the body halves 424*a* and 424*b* define a knife channel 427 (FIG. 20).

Each body half 424*a* and 424*b* defines a plurality of retention slots 430 which are aligned in two linear rows. The retention slots 430 open onto a tissue contact surface 430*a* of a respective body half 424*a*, 424*b*. Alternatively, additional rows of retention slots 430 may be provided in each body half 424*a*, 424*b*.

Referring to FIGS. 22-27, body half 424*a* is a mirror image of body half 424*b*. As such, only body half 424*a* will be described in further detail herein. Body half 424*a* defines a plurality of recesses 432 which open onto inner and outer sidewalls 436*a* and 436*b*, respectively of body half 424*b*. Each recess 432 of the plurality of recesses 432 communicates with a retention slot 430 and houses a magazine 434 of staples 435 including a staple 435*a* aligned with a retention slot 430. Although each magazine 434 of staples 435 is illustrated to include five staples 435, it is envisioned that each magazine 434 of staples 435 can include a different number of staples 435, e.g., 2 or more. The recesses 432 are in lateral alignment with a respective retention slot 430. Each recess 432 defines a U-shaped track which allows the magazine 434 of staples 435 to slide toward the retention slot 430 as the staples 435 are ejected. The end of each recess 432 adjacent each sidewall 436 is enclosed by the cartridge support channel 440 which retains each staple magazine 434 within its respective recess 432.

Body half 424*a* supports a plurality of first biasing members 442 and a plurality of second biasing members 444. One first biasing member 442 and one second biasing member 444 is associated with each recess 432 and each staple magazine 434. The first biasing member 442 is similar to biasing member 246 described above and includes a U-shaped resilient member having a backspan 442*a* and a pair of legs 442*b*. The legs 442*b* of each of the first biasing members 442 extend through openings 446 (FIG. 24) and into the recess 432. When inserted through the openings 446, the legs 442*b* are positioned to engage the legs 435*c* of the outermost staple 435*b* (FIG. 25) nearest a sidewall 436*a*, 436*b* to urge the staple magazine 434 inwardly towards a respective retention slot 430.

Figure 22A:
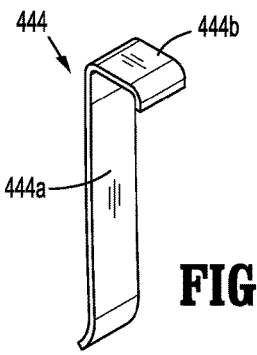
FIG. 22A is a first side perspective view of a second biasing member of the cartridge assembly shown in FIG. 22.
Figure 23:
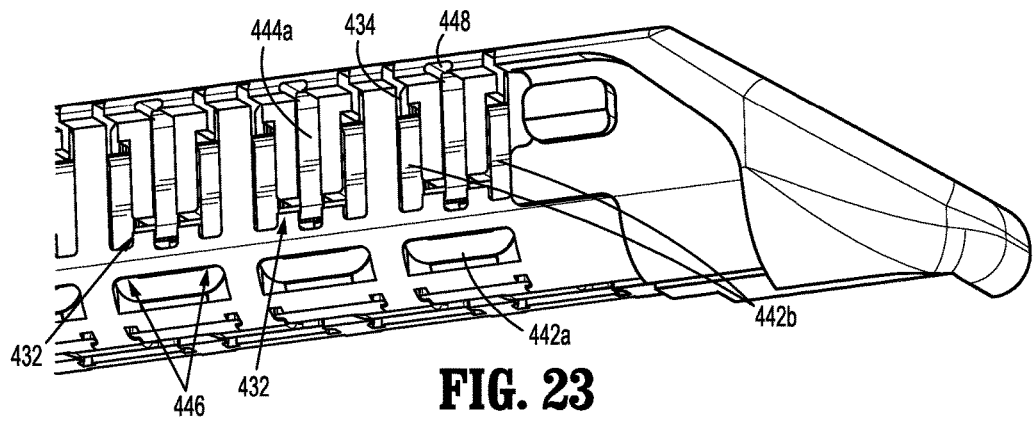
FIG. 23 is a side perspective view of the cartridge body half shown in FIG. 21 with a cartridge support channel removed.
Figure 24:
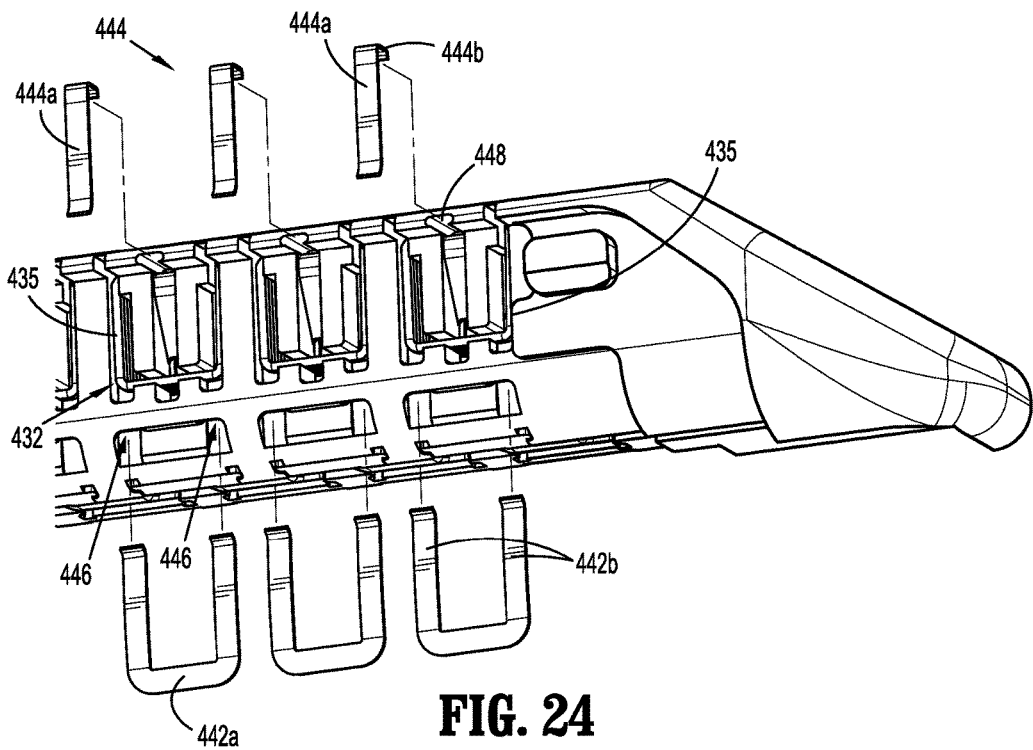
FIG. 24 is a side perspective view of the cartridge body half shown in FIG. 23 with the first and second biasing members separated from the cartridge body half.
Figure 25:
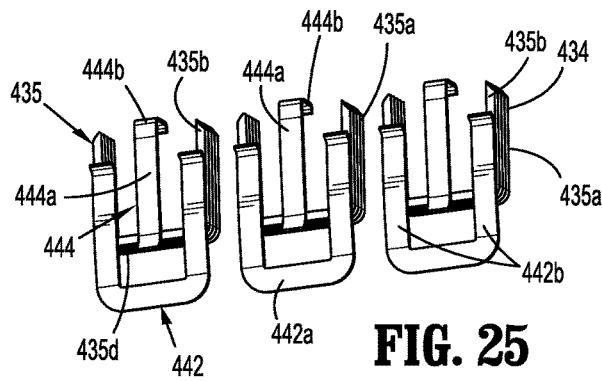
FIG. 25 is a side perspective view of the staple magazine shown in FIG. 22 in association with the first and second biasing members.

Each of the second biasing members 444 (FIG. 22A) includes a single resilient leg 444*a* and a connecting portion 444*b* which is configured to secure the second biasing member 444 within the body half 424*a*. The connecting portion 444*b* includes a transverse member 444*b* which is received within a cutout 448 (FIG. 26) formed in the body half 424*a* to secure the second biasing member 444 within a central portion of each recess 432. The second biasing member 444 is supported within the body half 424*a* such that the resilient leg 444*a* engages the backspan 435*d* of the staple 435*b* of the magazine 434.

Figure 26:
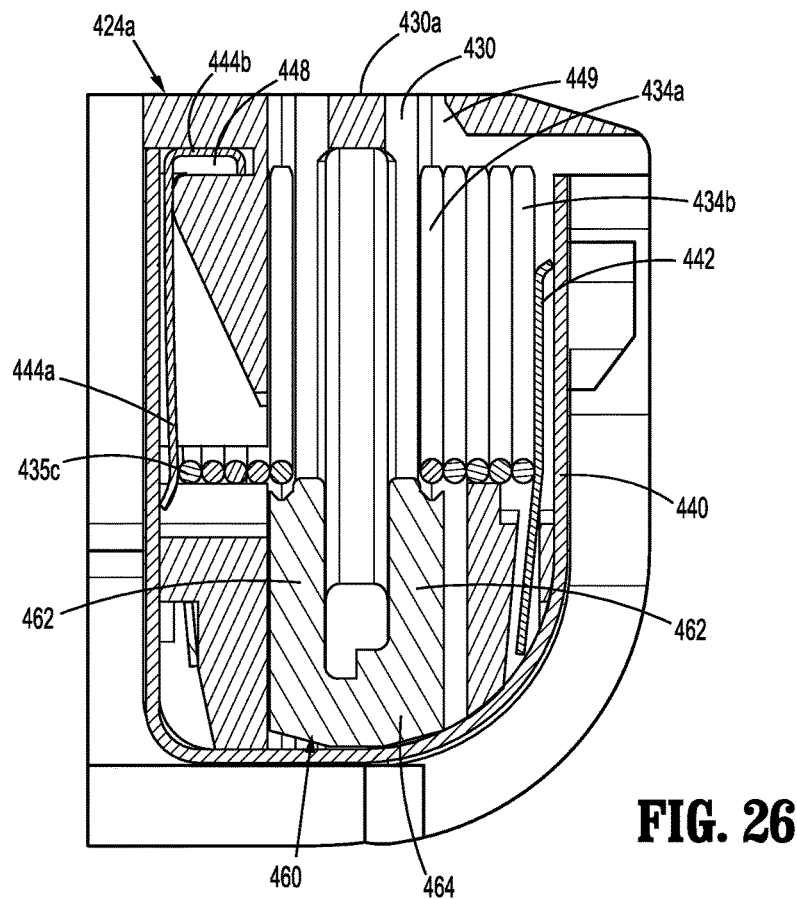
FIG. 26 is a cross-sectional view taken along section line 26-26 of FIG. 21 with a full staple magazine.
Figure 27:
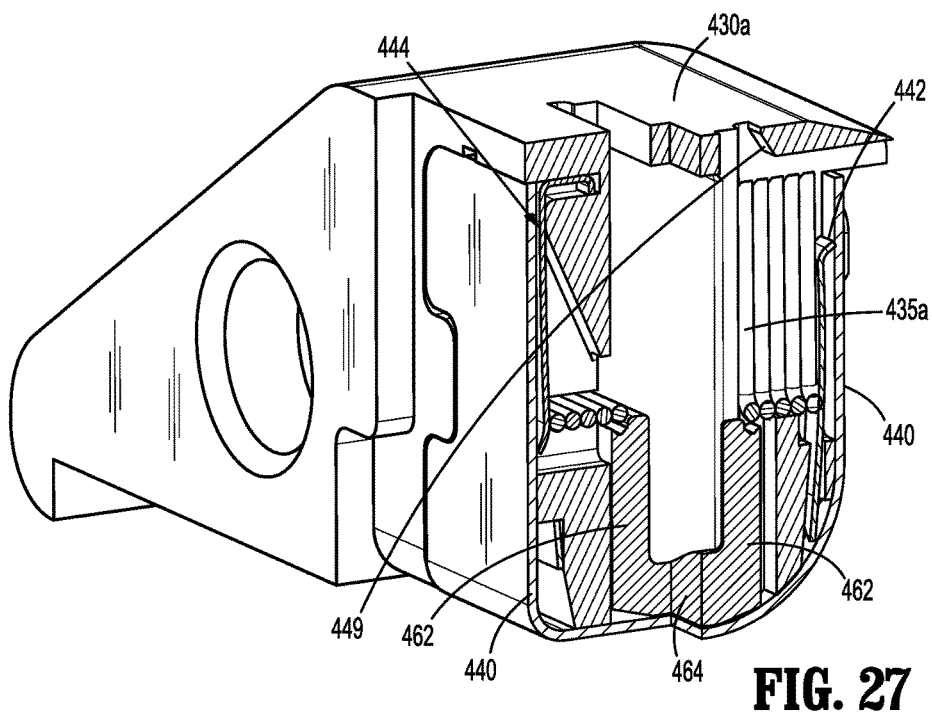
FIG. 27 is a side perspective, partial cross-sectional view of the cartridge body half shown in FIG. 26 with a full staple magazine.
Figure 28:
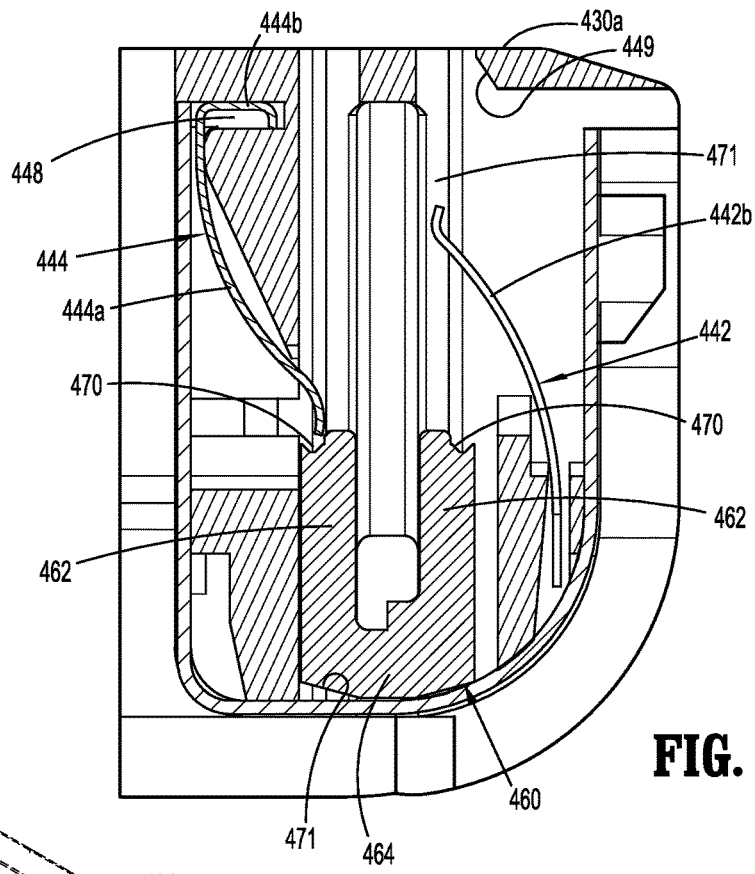
FIG. 28 is a cross-sectional view taken through the cartridge body half of FIG. 21 with a depleted staple magazine.
Figure 29:
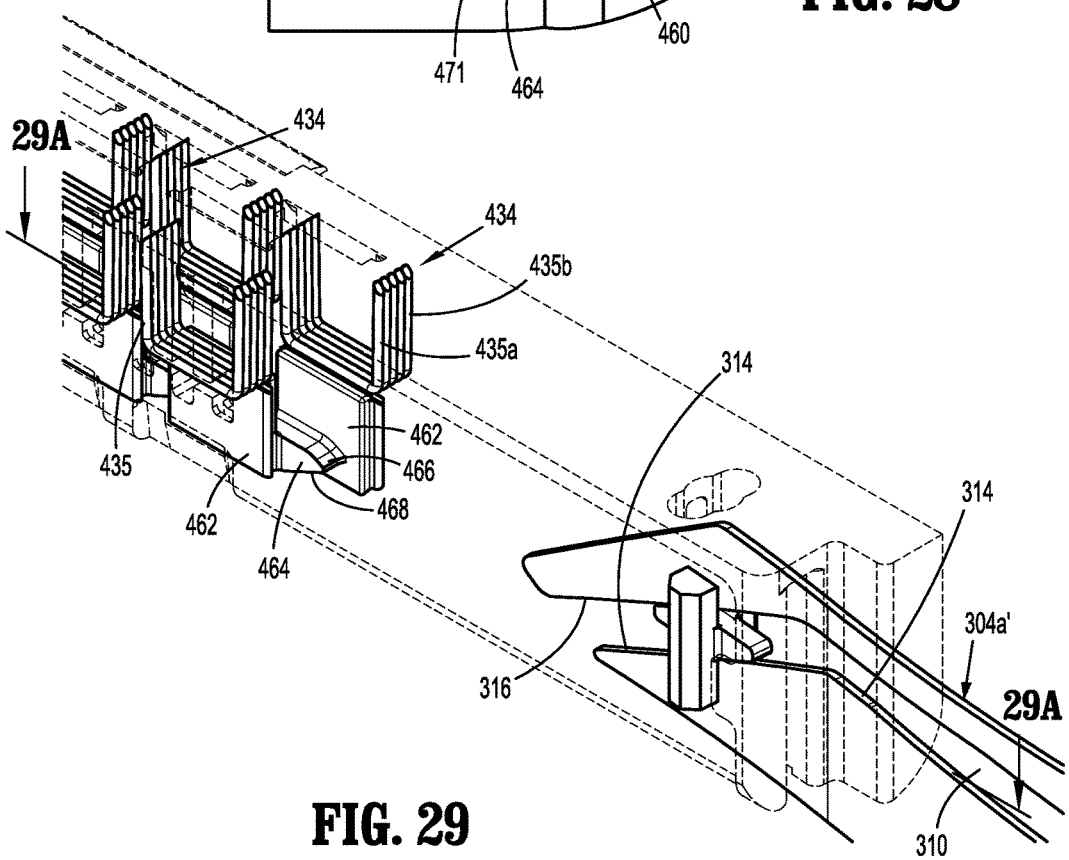
FIG. 29 is a side perspective view of the cartridge body half of the tool assembly shown in FIG. 1 with the cartridge body half shown in phantom, and a distal end of the firing cam assembly positioned proximally of the staple pushers.
Figure 30:
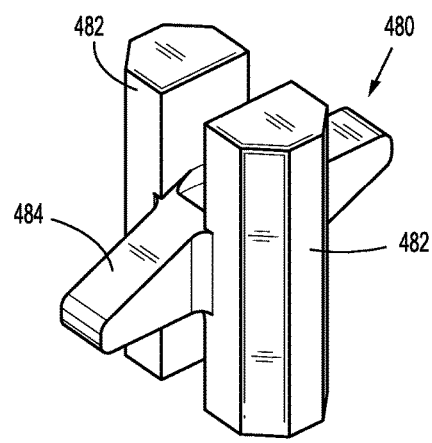
FIG. 30 is a side perspective view of a cam separation of a cartridge body half of the cartridge assembly shown in FIG. 22.

Referring to FIGS. 26-29B, the body half 424*a* supports a plurality of pushers 460. Each of the pushers 460 is substantially similar to pusher 108 described above (FIG. 5) and includes a pair of pusher plates 462 interconnected by a pusher base 464. The pusher base 464 defines an upper cam surface 466 and a lower cam surface 468 (FIG. 29). Each pusher plate 462 is slidably positioned in a respective retention slot 430 from a lower position to a raised or fired position to eject a staple 435 of the magazine 434 from a retention slot 430. As illustrated in FIG. 26, an inner tapered wall 449*a* of the body half 424*a* defines a lead-in chamber 449 to guide the staples 435*a* from the retention slots 430 through the tissue contact surface 430*a*.

Referring to FIG. 28, an upper surface of each pusher plate 462 defines a notch 470. When the last staple 435*b* of the staple magazine 434 is ejected from its respective retention slot 430 and the pusher 460 is returned to the lower position as will be discussed below, the resilient leg 444*a* of the second biasing member 444 springs into the retention slot 430 to obstruct movement of the pusher plate 462 within the retention slot 430 back to the raised position. More specifically, the leg 444*a* of the second biasing member 444 moves to a position aligned with the notch 470 to prevent movement of the pusher 460 back to the raised position as will be discussed in further detail below.

The tool assembly 418 includes a firing cam assembly similar to firing cam assembly 300 (FIGS. 14-16) as discussed above with respect to tool assembly 18. The firing cam assembly 300 for use with tool assembly 418 includes two firing cams 304*a*' (only one firing cam 304*a*' is shown). As illustrated in FIG. 29, each of the firing cams 304*a*' includes a first blade 314*a* and a second blade 316*a* which are separated by a camming slot 310. The camming slot 310 receives the pusher base 464 of a respective pusher 460 as the firing cam 304*a*' is moved within firing cam channel 471 (FIG. 28) to control movement of the pusher 460 between the lower position and the raised or fired position. More specifically, when the firing cam 304*a*' is translated distally through the firing cam channel 471 of the cartridge body half 424*a*, the pusher base 464 is received within and translates along camming slot 310 of firing cam 304*a*'. As this occurs, lower cam surface 468 (FIG. 29) of pusher base 464 rides up along firing cam surface 314 of the first blade 314*a* of the firing cam 304*a*' to move the pusher 460 from the lower position to the raised or fired position. Subsequently, when the firing cam 304*a*' is translated proximally within firing cam channel 471, the upper cam surface 466 of the pusher base 464 is engaged by a retracting cam surface 316 of the second blade 316*a* of the firing cam 304*a*' to return the pusher 460 to the lower position.

Referring again to FIGS. 29-31, the cartridge assembly 420 further includes a cam separator 480 associated with each firing cam 304*a*'. Each cam separator 480 (FIG. 30) includes a pair of guide members 482 which are interconnected by a cam member 484. The cam separator 480 is slidably positioned within a vertical channel 490 (FIG. 21) formed in the body halves 424*a*, 424*b*. As such, each cam separator 480 is axially fixed but vertically movable within the cartridge body half 424*a*, 424*b*. The cam separator 480 is positioned such that the cam member 484 is received within a distal end of the camming slot 310 of a respective firing cam 304*a*' (FIG. 29) of the firing cam assembly when the firing cam 304*a*' is in a retracted position. As the firing cam 304*a*' is moved from the retracted position to the advanced position, the cam separator 480 will be moved from a lower position to a raised position within the vertical channel 490 of the body halves 424*a*, 424*b*. The cam separator 480 maintains proper separation of the first and second blades 314*a* and 316*a*, of the firing cam 304*a*' prior to and during advancement of the firing cam 304*a*'.

Referring to FIG. 29, the tool assembly 418 functions in a manner substantially as described above with regard to tool assembly 18. More specifically, when the stapling device 10 (FIG. 10) is actuated to advance the firing cam 304*a*' by, for example, moving movable handle 26 towards stationary handle 26 in relation to stationary handle 24 (FIG. 1), the firing cam 304a' moves distally within cam channel 471 of body half 424a such that the pusher base 464 of pusher 460 is received within camming slot 310 of the firing cam 304a'. It is noted that the presently disclosed tool assembly is also suitable for use with motorized or robotically actuated surgical devices. As the firing cam 304a' moves distally in relation to each pusher 460, the firing cam surface 314 of firing cam 304a' is positioned beneath the pusher base 464 and urges the pusher base 464 and thus, the pusher 460, upwardly. As the pusher 460 moves upwardly, the pusher plates 462 move upwardly within the retention slots 430 to force a staple 435a of the staple magazine 434 upwardly and out of the retention slot 430. When the pusher 460 is in its raised or firing position, the pusher plates 462 block entry of the next staple 435 of the staple magazine 434 from entering the retention slot 430.

Figure 31:
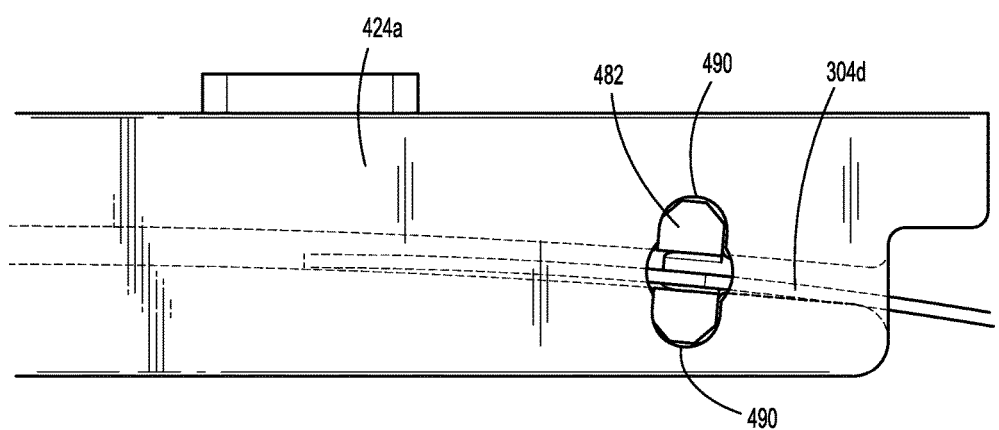
FIG. 31 is a schematic top view of a cartridge body half illustrating the cam separator and cam drive bar and the cam pathway in phantom.

When the firing cam 304a' is retracted within the firing cam channel 471, the pusher base 464 of each pusher 460 moves along camming slot 310 to move the pusher 460, and thus, the pusher plates 462, downwardly to the lower position. When the pusher plates 462 pass by recesses 432 (FIG. 27), the first and second biasing members 442 and 444 push the staple magazine 434 towards the retention slots 430 to place the next staple 435 of the staple magazine 434 into alignment with the retention slot 430. This process can be repeated to eject each of the staples 435 from the staple magazine 434. As shown in FIGS. 29 and 31, the cam separator 480 maintains proper spacing between the first blade 314a and the second blade 314b of the firing cam 304a' when the firing cam 304a' is in the retracted position.

Referring to FIG. 28, after the last staple 435b of each staple magazine 434 is ejected from the body half 424a, the resilient leg 444a of the second biasing member 444, which no longer engages a staple backspan 435d springs into a position above the notch 470 formed in each pusher plate 462 of the pusher 460 to prevent movement of the pusher 460 from the lower position back to the raised position. Since the pushers 460 are locked in the lower position, movement of the firing cam 304a' through the cartridge body half 424a is prevented and the tool assembly 418 is locked out.

Figure 14:
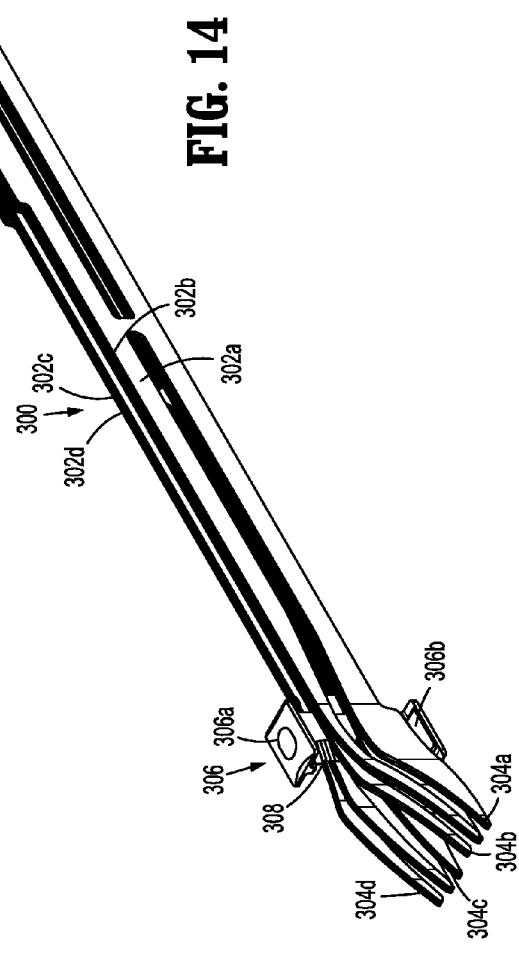
FIG. 14 is a perspective view of the firing cam assembly of FIG. 13.

As discussed above, the cartridge assembly 420 includes first and second cartridge body halves 424a and 424b. Cartridge body half 424b also includes a firing cam 304a'. Although not shown, the tool assembly 418 also includes a firing cam assembly such as shown in FIG. 14 which includes the firing cams 304a' (FIG. 29), a central drive member 306 and a knife 308. Alternatively, the cartridge assembly 420 may only have one or more rows of staples which are supported in a cartridge body as described above. The cartridge assembly need not include a knife.

It is contemplated that individual features of the above described embodiments may be combined without departing from the scope of the present disclosure. Although the illustrative embodiments of the present disclosure have been described herein with reference to the accompanying drawings, the above description, disclosure, and figures should not be construed as limiting, but merely as exemplifications of particular embodiments. For example, although the tool assembly 18, 418 is described as forming a portion of a DLU, it is envisioned that the tool assembly 18, 418 can be integrally secured to the body 14 of a surgical device 10 (FIG. 1). It is to be understood, therefore, that the disclosure is not limited to the precise embodiments described herein, and that various other changes and modifications may be effected by one skilled in the art without departing from the scope or spirit of the present disclosure.

The invention claimed is:

1. A tool assembly comprising:
    an anvil assembly
    a cartridge assembly movably supported in relation to the anvil assembly, the cartridge assembly including a cartridge body defining a tissue contact surface and a plurality of retention slots which open onto the tissue contact surface, the cartridge body defining a plurality of recesses, each of the recesses being associated with one of the plurality of retention slots;
    a staple magazine positioned within each of the recesses, the staple magazine including a plurality of staples;
    at least one biasing member supported adjacent each of the recesses, the at least one biasing member being positioned to urge the staple magazine towards a respective one of the retention slots;
    a plurality of pushers movably supported within the cartridge body between a lower position and a raised position, each of the plurality of pushers being positioned to engage and eject at least one of the staples of the staple magazine from the retention slot;
    wherein the at least one biasing member is positioned to prevent movement of the pusher from the lower position to the raised position after the plurality of staples of the staple magazine have been ejected from a respective one of the retention slots.

2. The tool assembly of claim 1, wherein each of the pushers includes at least one pusher plate, each of the at least one pusher plates being movable within a respective one of the retention slots to eject one of the plurality of staples of the staple magazine from the cartridge body.

3. The tool assembly of claim 2, wherein each of the at least one pusher plates defines a notch and the at least one biasing member includes a leg, the leg being movable into alignment with the notch after the plurality of staples of the staple magazine has been ejected from the retention slot to obstruct movement of the pusher from the lower position to the raised position.

4. The tool assembly of claim 1, wherein the cartridge body includes a first body half and a second body half, each of the first and second body halves defining a plurality of retention slots and a plurality of recesses, wherein each of the plurality of recesses houses a staple magazine.

5. The tool assembly of claim 4, further including a carrier defining a carrier channel, wherein the first and second body halves of the cartridge body are supported within the carrier channel.

6. The tool assembly of claim 5, further including a first support channel and a second support channel, the first and second body halves being positioned within the first and second support channels and the first and second support channels being supported in the carrier channel of the carrier.

7. The tool assembly comprising:
    an anvil assembly
    a cartridge assembly movably supported in relation to the anvil assembly, the cartridge assembly including a cartridge body defining a tissue contact surface and a plurality of retention slots which open onto the tissue contact surface, the cartridge body defining a plurality of recesses, each of the recesses being associated with one of the plurality of retention slots;
    a staple magazine positioned within each of the recesses, the staple magazine including a plurality of staples;

at least one biasing member supported adjacent each of the recesses, the at least one biasing member being positioned to urge the staple magazine towards a respective one of the retention slots;

a plurality of pushers movably supported within the cartridge body between a lower position and a raised position, each of the plurality of pushers being positioned to engage and eject at least one of the staples of the staple magazine from the retention slot;

wherein the at least one biasing member is positioned to prevent movement of the pusher from the lower position to the raised position after the plurality of staples of the staple magazine have been ejected from a respective one of the retention slots; and wherein the at least one biasing member includes a first biasing member and a second biasing member, the first biasing member being supported within the cartridge body to engage legs of a respective one of the plurality of staples and the second biasing member being supported within the cartridge body to engage a backspan of the respective staple of the plurality of staples.

8. The tool assembly of claim 7, wherein the first biasing member is U-shaped and includes a pair of legs positioned to engage the legs of the respective one of the plurality of staples.

9. The tool assembly of claim 7, wherein the second biasing member is positioned to obstruct movement of the pusher after the plurality of staples of the staple magazine have been ejected from the respective one of the retention slots.

10. The tool assembly of claim 9, wherein each of the pushers includes at least one pusher plate, each of the at least one pusher plates being movable within a respective one of the retention slots to eject one of the plurality of staples of the staple magazine from the cartridge body.

11. The tool assembly of claim 10, wherein each of the at least one pusher plates defines a notch and the at least one biasing member includes a leg, the leg being movable into alignment with the notch after the plurality of staples of the staple magazine have been ejected from the retention slot to obstruct movement of the pusher from the lower position back to the raised position.

12. The tool assembly comprising:
an anvil assembly
a cartridge assembly movably supported in relation to the anvil assembly, the cartridge assembly including a cartridge body defining a tissue contact surface and a plurality of retention slots which open onto the tissue contact surface, the cartridge body defining a plurality of recesses, each of the recesses being associated with one of the plurality of retention slots;
a staple magazine positioned within each of the recesses, the staple magazine including a plurality of staples;
at least one biasing member supported adjacent each of the recesses, the at least one biasing member being positioned to urge the staple magazine towards a respective one of the retention slots;
a plurality of pushers movably supported within the cartridge body between a lower position and a raised position, each of the plurality of pushers being positioned to engage and eject at least one of the staples of the staple magazine from the retention slot;
wherein the at least one biasing member is positioned to prevent movement of the pusher from the lower position to the raised position after the plurality of staples of the staple magazine have been ejected from a respective one of the retention slots; and
further including a firing cam having a first blade and a second blade which define a camming slot, the firing cam being movable between a retracted position and an advanced position within the cartridge body, the camming slot being configured to receive the plurality of pushers to move the pushers between the lower position and the raised position as the firing cam translates between the retracted position and the advanced position.

13. The tool assembly of claim 12, wherein each of the plurality of pushers includes at least one pusher plate which is movably supported within a respective one of the plurality of retention slots and a pusher base which is positioned to be received within the camming slot of the firing cam.

14. The tool assembly of claim 13, further including a cam separator, wherein the cartridge body defines a vertical channel, the cam separator being supported for movement within the vertical channel and being positioned within the camming slot of the firing cam when the firing cam is in the retracted position to maintain separation of the first and second blades of the firing cam.

15. A tool assembly comprising:
an anvil assembly;
a cartridge assembly including a cartridge body defining a plurality of retention slots and a plurality of recesses, each of the plurality of recesses housing a staple magazine including a plurality of staples;
a plurality of pushers, each of the plurality of pushers being associated with at least one of the retention slots;
a firing cam movable between a retracted position and an advanced position within the cartridge body, the firing cam having a first blade and a second blade, the first and second blades defining a camming slot, the caming slot being configured to receive the plurality of pushers to effect movement of the pushers between a lower position and a raised position; and
a cam separator supported within a vertical channel defined in the cartridge body, the cam separator being positioned within the camming slot of the firing cam when the firing cam is in a retracted position to maintain spacing between the first and second blades.

16. The tool assembly of claim 15, further including at least one biasing member supported adjacent each of the recesses, the at least one biasing member being positioned to urge the staple magazine towards a respective one of the retention slots.

17. The tool assembly of claim 16, wherein the at least one biasing member is positioned to obstruct movement of the pusher from the lower position to the raised position after the plurality of staples of the staple magazine have been ejected from a respective one of the retention slots.

18. The tool assembly of claim 17, wherein each of the pushers includes at least one pusher plate, each of the at least one pusher plates being movable within a respective one of the retention slots to eject one of the plurality of staples of the staple magazine from the cartridge body.

19. The tool assembly of claim 18, wherein each of the at least one pusher plates defines a notch and the at least one biasing member includes a leg, the leg being movable into alignment with the notch after the plurality of staples of the staple magazine have been ejected from the retention slot to obstruct movement of the pusher from the lower position to the raised position.

* * * * *